(12) United States Patent
Begue et al.

(10) Patent No.: US 8,236,850 B2
(45) Date of Patent: Aug. 7, 2012

(54) DIMERIC DERIVATIVES OF ARTEMISININ AND APPLICATION IN ANTICANCER THERAPY

(75) Inventors: Jean-Pierre Begue, Paris (FR); Danielle Bonnet-Delpon, Paris (FR); Benoît Crousse, Igny (FR); Fabienne Grellepois, Reims (FR); Constance Chollet, Montrouge (FR); Jacques Fahy, Labruguiere (FR); Céline Mordant, Saint Julien En Genevois (FR)

(73) Assignees: Pierre Fabre Medicament, Boulogne-Billancourt (FR); Centre National de la Recherche Scientifique, Paris (FR); Universite Paris-Sud 11, Orsay (FR)

( * ) Notice: Subject to any disclaimer, the term of this patent is extended or adjusted under 35 U.S.C. 154(b) by 0 days.

(21) Appl. No.: 12/808,828

(22) PCT Filed: Dec. 22, 2008

(86) PCT No.: PCT/EP2008/068133
§ 371 (c)(1),
(2), (4) Date: Jun. 17, 2010

(87) PCT Pub. No.: WO2009/080805
PCT Pub. Date: Jul. 2, 2009

(65) Prior Publication Data
US 2010/0266570 A1    Oct. 21, 2010

(30) Foreign Application Priority Data

Dec. 21, 2007   (FR) ..................... 07 60266

(51) Int. Cl.
*A61K 31/337*   (2006.01)
*C07D 493/16*   (2006.01)
*C07D 321/02*   (2006.01)
(52) U.S. Cl. .......... 514/450; 549/354; 549/348
(58) Field of Classification Search .......... 549/348, 549/354; 514/450
See application file for complete search history.

(56) References Cited

U.S. PATENT DOCUMENTS

| | | | |
|---|---|---|---|
| 5,856,351 A * | 1/1999 | Zheng et al. | 514/450 |
| 6,160,004 A * | 12/2000 | Posner et al. | 514/450 |
| 7,417,155 B2 * | 8/2008 | Begue et al. | 549/348 |
| 2005/0070595 A1 * | 3/2005 | O'Neil et al. | 514/452 |
| 2009/0082426 A1 * | 3/2009 | Commercon et al. | 514/450 |

FOREIGN PATENT DOCUMENTS

| | | |
|---|---|---|
| WO | WO 00/42046 A1 | 7/2000 |
| WO | WO 03/035651 A2 | 5/2003 |
| WO | WO 03/095444 A1 | 11/2003 |

OTHER PUBLICATIONS

Jung, Antitumor Activity of Novel Deoxoartemisinin Monomers, Dimers, and Trimer, 2003, J. Med. Chem, vol. 46, p. 987-994.*

Patani, Bioisosterism: A Rational Approach in Drug Design, Chem. Rev., 1996, vol. 96, p. 3147-3176.*

Beekman et al, "Stereochemistry-Dependent Cytotoxicity of Some Artemisinin Derivatives," Journal of Natural Products, vol. 60, No. 4, pp. 325-330, Apr. 1997.

Begue et al., "Fluoroarteminisinins: Metabolically More Stable Antimalarial Artemisinin Derivatives," ChemMedChem 2007, vol. 2, Wiley-VCH Verlag GmbH & Co. KGaA, Weinheim, pp. 608-624, 2007.

Ekthawatchai et al., "C-16 Artemisinin Derivatives and Their Antimalarial and Cytotoxic Activities: Syntheses of Artemisinin Monomers, Dimers, Trimers, and Tetramers by Nucleophilic Additions to Artemisitene," J. Med. Chem, vol. 44, No. 26, pp. 4688-4695, Nov. 22, 2001.

Grellepois et al., "Orally Active Antimalarials: Hydrolytically Stable Derivatives of 10-Trifluoromethyl Anhydrodihydroartemisinin," J. Med. Chem., vol. 47, No. 6, pp. 1423-1433, Feb. 11, 2004.

Grellepois et al., "Synthesis of New Artemisinin-Derived Dimers by Self-Cross-Metathesis Reaction," Organic Letters, vol. 7, No. 23, pp. 5219-5222, XP-002477156, Aug. 25, 2005.

International Search Report dated Mar. 4, 2009 for Application No. PCT/EP2008/068133.

O'Neill et al., "A Medicinal Chemistry Perspective on Artemisinin and Related Endoperoxides," Journal of Medicinal Chemistry, vol. 47, No. 12, pp. 2945-2964, Jun. 3, 2004.

Posner et al., "Antimalarial, Antiproliferative, and Antitumor Activities of Artemisinin-Derived, Chemically Robust, Trioxane Dimers," Journal of Medical Chemistry, vol. 42, No. 21, pp. 4275-4280, XP001061756, Oct. 21, 1999.

(Continued)

*Primary Examiner* — Noble Jarrell
*Assistant Examiner* — Karen Cheng
(74) *Attorney, Agent, or Firm* — Birch, Stewart, Kolasch & Birch, LLP

(57) ABSTRACT

The present invention relates to dimeric derivatives of 10-trifluoromethylated artemisinin of formula (I): or a pharmaceutically acceptable salt thereof with $B_1$ and $B_2$ selected from C=O, CHOH and $CH_2$, as well as to their use in treating cancer and to their preparation method.

(I)

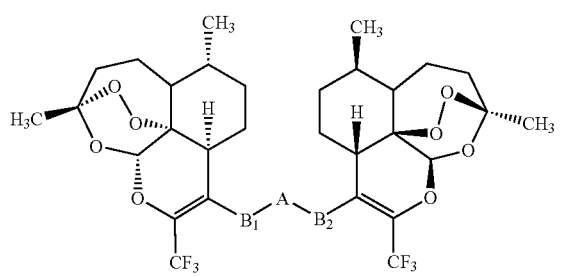

8 Claims, No Drawings

OTHER PUBLICATIONS

Posner et al., "Trioxane Dimers Have Potent Antimalarial, Antiproliferative and Antitumor Activities in Vitro," Bioorganic & Medicinal Chemistry, vol. 5, No. 7, XP-002409018, pp. 1257-1265, 1997.

Ramesha et al., "Benzyltriethylammonium Tetrathiomolybdate: An Improved Sulfur Transfer Reagent for the Synthesis of Disulfides," Synthetic Communications, vol. 22, No. 22, pp. 3277-3284, 1992.

Sun et al., "Antitumor Activities of 4 Derivatives of Artemisic Acid and Artemisinin B in Vitro," Acta Pharmacologica Sinica, vol. 13, No. 6, pp. 541-543, Nov. 1992.

Woerdenbag et al., "Cytotoxicity of Artemisinin-Related Endoperoxides to Ehrlich Ascites Tumor Cells," Journal of Natural Products, vol. 56, No. 6, pp. 849-856, Jun. 1993.

* cited by examiner

DIMERIC DERIVATIVES OF ARTEMISININ AND APPLICATION IN ANTICANCER THERAPY

The present invention relates to dimeric derivatives of 10-trifluoromethyl artemisinin connected through their carbons in position 16 as well as to their use in the treatment against cancer.

Cytotoxic properties of artemisinin derivatives were demonstrated in 1992 [*Acta Pharmacol. Sin.*, 13, 541-3, (1992)], thereby imparting to these compounds a potential use as an anticancer agent. It then appeared that dimeric derivatives of artemisinin had cytotoxic activities sometimes higher than that of the corresponding monomers [*J. Nat. Prod.*, 56, 849-56, (1993), *J. Nat. Prod.*, 60, 325-30, (1997)].

Therefore, many studies aiming at preparing novel artemisinin dimers were undertaken by several research teams worldwide. Most of these dimers are C-10 dimers, i.e. connected through their carbon in position 10, of ether derivatives of dihydroartemisinin [*Bioorg. Med. Chem.*, 5, 1257-65, (1997)] or of non-ketalic metabolically more stable analogs, where the exocyclic oxygen atom of the ketal function has been replaced with a $CH_2$ group (group X on the diagram below) [*J. Med. Chem.*, 42, 4275-80, (1999)]. C-16 dimers are also described [*J. Med. Chem.*, 44, 4688-95, (2001)] but some of them prove to be unstable and spontaneously decompose in solution or during their storage at room temperature. These different families are schematized herein below:

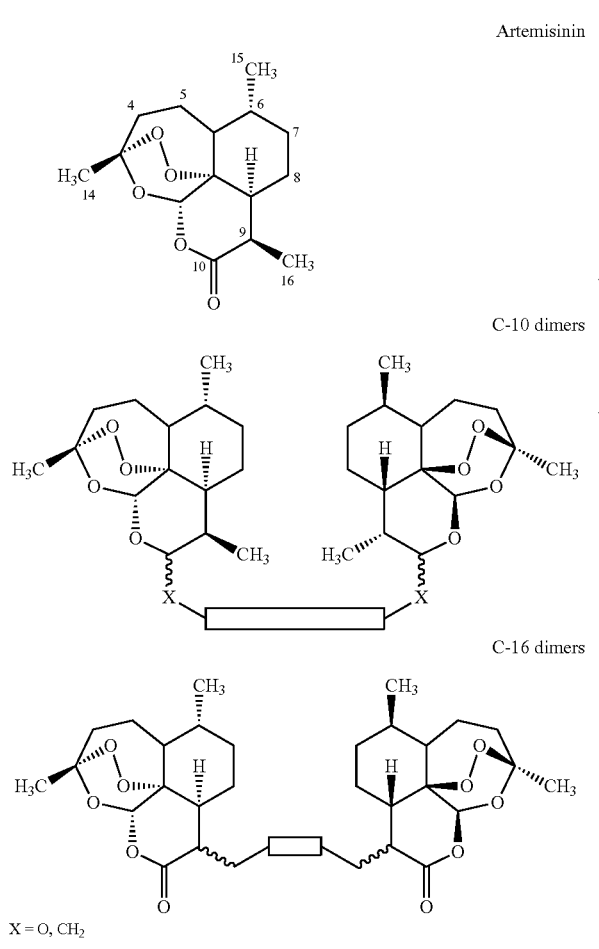

Artemisinin and its derivatives, such as artemether or sodium artesunate for the most known, are widely used in treating malaria. However, the main limitation of these derivatives lies in the low bioavailability of the artemisinin nucleus, the ketal function of which is rapidly hydrolyzed in the organism, then leading to inactive metabolites [*J. Med. Chem.*, 47, 2945-64, (2004)].

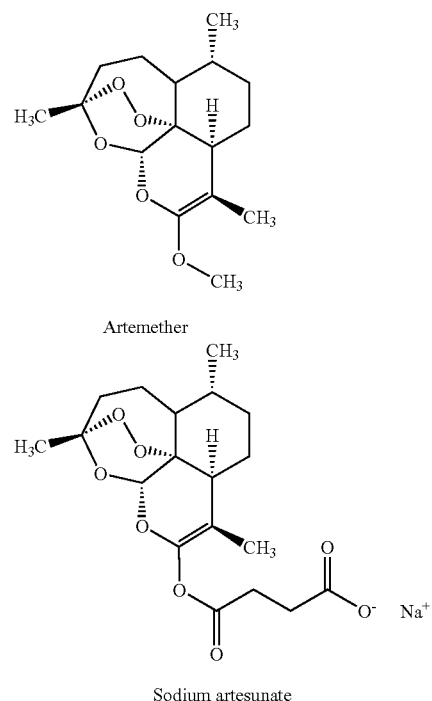

Within the scope of the search for novel stable artemisinin derivatives for treating malaria, studies conducted at the Bio-CIS Laboratory of the Faculty of Pharmacy of Chatenay-Malabry have resulted in the synthesis of 10-trifluoromethylated artemisinin derivatives (WO 03/035651). The introduction of a trifluoromethyl group stabilizes the ketalic function, which has the consequence of very significantly increasing the stability of these compounds and extending their period of action, notably upon administration of the compounds orally.

A recent review accurately details the advantages of trifluoromethylated derivatives of artemisinin both chemically and pharmacologically [J.-P. Bégué, D. Bonnet-Delpon, *ChemMedChem*, 2, 608-24, (2007)].

The object of the present invention is dimeric derivatives of 10-trifluoromethylated artemisinin of formula I:

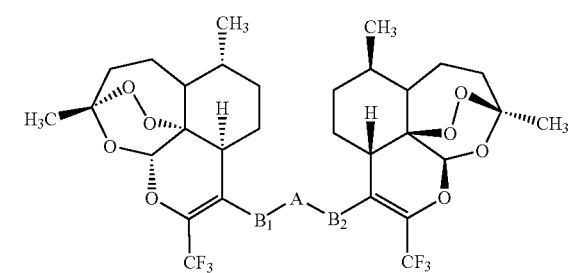

(I)

or a pharmaceutically acceptable salt thereof,
for which:

$B_1$ and $B_2$ are identical or different and selected from $C=O$, CHOH and $CH_2$, advantageously from $C=O$ and $CH_2$, and preferably each represent a $CH_2$ group, and A represents:
- a divalent group selected from —S—, —S—S—, —SO—, —SO$_2$—, —Se—Se—, —O—P(O)(OR1)-O—, —NR2-, —O—R4-and —O—NR2-, and preferably from —S—, —S—S—, —SO—, —SO$_2$—, —Se—Se—, —O—P(O)(OR1)-O— and —O—NR2-, with
  - R1 representing a hydrogen, a $C_1$-$C_6$ alkyl group or an optionally substituted aryl group,
  - R2 representing a hydrogen, a $C_1$-$C_6$ alkyl group optionally substituted with an $NH_2$ group, a $C_2$-$C_6$ alkenyl group, a $C_2$-$C_6$ alkynyl group, a $C_3$-$C_8$ cycloalkyl group, an aryl-($C_1$-$C_6$)-alkylene group, an optionally substituted aryl group, or a —COR3, —CO$_2$R3 or —SO$_2$R3 group,
  - R3 representing a hydrogen, a $C_1$-$C_6$ alkyl group, a $C_3$-$C_8$ cycloalkyl group, an aryl-($C_1$-$C_6$)-alkylene group or an optionally substituted aryl group, and
  - R4 representing a $C_1$-$C_6$ alkylene group, a $C_2$-$C_6$ alkenylene group or a $C_2$-$C_6$ alkynylene group, or
- an X—Y—Z group for which:
  - X and Z are identical or different and are selected from O, S, NR2, with R2 as defined earlier, and a heterocycle comprising at least one nitrogen atom bound to $B_1$ or $B_2$, and
  - Y is selected from:
    - a $C_1$-$C_6$ alkylene group, a $C_3$-$C_8$ cycloalkylene group and a $C_2$-$C_6$ alkenylene group,
    - a —CO—Y1-CO— group wherein Y1 represents a $C_1$-$C_6$ alkylene group optionally substituted with an NHR2 group, with R2 as defined above, and preferably wherein Y1 represents a —(CH$_2$)$_q$— group, for which q represents an integer equal to 1, 2, 3 or 4,
    - a polyamine group of formula —[(CH$_2$)$_n$—NR2-(CH$_2$)$_m$]$_p$— for which R2 is as defined earlier and n, m and p represent independently of each other, an integer equal to 1, 2, 3 or 4, and
    - a —(CO)$_r$—(CH$_2$)$_s$—Y2-(CH$_2$)$_t$—(CO)$_u$— group for which:
      - r and u represent independently of each other an integer equal to 0 or 1,
      - s and t represent, independently of each other, an integer equal to 0, 1, 2, 3 or 4,
      - s, respectively t, cannot be equal to 0 if r, respectively u, is equal to 0 and
      - Y2 is selected from —S—, —S—S—, —SO—, —SO$_2$—, —Se—Se—, —O—P(O)(OR1)-O— with R1 as defined earlier, —NR2- with R2 as defined earlier, a $C_3$-$C_8$ cycloalkylene group and an optionally substituted heteroaromatic or aromatic ring.

The dimeric derivatives of the present invention thus have the advantages of fluorinated monomers as mentioned earlier while having good antitumoral properties.

By "$C_1$-$C_6$ alkyl" group, is understood in the sense of the present invention, a linear or branched monovalent saturated hydrocarbon chain, including 1-6 carbon atoms, such as for example a methyl, ethyl, propyl, isopropyl, butyl, tertio-butyl or further pentyl group. Advantageously, this is a methyl group.

By "$C_2$-$C_6$ alkenyl" group, is meant in the sense of the present invention, a linear or branched monovalent hydrocarbon chain including 1-6 carbon atoms, and comprising at least one double bond, such as for example a vinyl, allyl group, etc.

By "$C_2$-$C_6$ alkynyl" group, is meant in the sense of the present invention, a linear or branched monovalent hydrocarbon chain including 1-6 carbon atoms and comprising at least one triple bond, such as for example a propynyl group.

By "aryl group" or "aromatic ring", is meant in the sense of the present invention, a monovalent or divalent aromatic group preferably including 5-10 carbon atoms and comprising one or more fused rings such as for example a phenyl or naphthyl group, and advantageously a phenyl group. This aromatic group may optionally be substituted, notably with a halogen, a $C_1$-$C_6$ alkyl group as defined earlier, an —OR, —NRR' and/or —SO$_2$R group with R and R' designating independently of each other a hydrogen or a $C_1$-$C_6$ alkyl group as defined earlier.

By "heteroaromatic ring", is meant in the sense of the present invention, an aromatic group as defined above, for which one or more, preferably 1-4, carbon atoms are replaced with a heteroatom, in particular an oxygen, a nitrogen or a sulfur, such as for example a pyridinyl, pyrimidinyl, pyridazinyl, pyrazinyl, indolyl, thiazolyl, pyrazolyl, imidazolyl, triazolyl, furanyl, thienyl or further pyrrolyl group. Advantageously, this will be a pyridinyl or thienyl group. This heteroaromatic ring may optionally be substituted notably with a halogen, a $C_1$-$C_6$ alkyl group as defined earlier, an —OR, —NRR' and/or —SO$_2$R group with R and R' designating, independently of each other, a hydrogen or a $C_1$-$C_6$ alkyl group as defined earlier.

By "heterocycle", is meant in the sense of the present invention, an aromatic, unsaturated, or saturated cyclic hydrocarbon compound comprising one or more fused rings, preferably one or two rings or even preferably a single ring, and comprising 5-10 ring atoms, for which one or more ring carbon atoms have been replaced with one or more heteroatoms, advantageously 1-4 and even more advantageously 1-3, such as for example sulfur, nitrogen or oxygen atoms, at least one of these heteroatoms being a nitrogen (which may bind to $B_1$ or $B_2$). This may be in particular a morpholinyl, piperazinyl, piperidinyl, pyrrolidinyl, pyrrolyl, indolyl, tetrazolyl or further triazolyl group. Advantageously, this is a piperazinyl or triazolyl group such as a 1,2,3-triazolyl.

The term of "halogen" designates fluorine, bromine, chlorine or iodine.

By "$C_3$-$C_8$ cycloalkyl" group, is meant in the sense of the present invention, a saturated hydrocarbon cyclic group including 3-8 carbon atoms, such as for example a cyclopropyl, cyclohexyl, cyclopentyl group, etc.

By "$C_1$-$C_6$ alkylene" group, is meant in the sense of the present invention, a linear or branched divalent saturated hydrocarbon chain comprising 1-6 carbon atoms, such as for example a methylene, ethylene, propylene, butylene, pentylene, hexylene group, etc.

By "$C_2$-$C_6$ alkenylene" group, is meant in the sense of the present invention, a linear or branched divalent hydrocarbon chain comprising 2-6 carbon atoms and at least one double bond, such as for example, a vinylene (ethenylene) or propenylene group.

By "$C_2$-$C_6$ alkynylene" group, is meant in the sense of the present invention, a linear or branched divalent hydrocarbon chain comprising 2-6 carbon atoms and at least one triple bond, such as for example a propynylene group.

By "$C_3$-$C_8$-cycloalkylene" group, is meant in the sense of the present invention, a divalent saturated hydrocarbon cyclic group comprising 3-8 carbon atoms, such as for example a cyclopropylene, 1,4-cyclohexylene, 1,3-cyclohexylene, 1,2-cyclopentylene group, etc.

By "aryl-($C_1$-$C_6$)-alkylene" group, is meant in the sense of the present invention, an aryl group as defined earlier bound via a $C_1$-$C_6$ alkylene group as defined above. Advantageously, this may be a benzyl group.

By "pharmaceutically acceptable salt", is meant notably a salt obtained from pharmaceutically acceptable acids or bases.

Among the pharmaceutically acceptable acids, mention may be made in a non-limiting way, of inorganic acids, such as hydrohalic acids, like hydrochloric and hydrobromic acids, sulfuric, nitric or even phosphoric acids, or organic acids, such as acetic, propionic, benzoic, lactic, pyruvic, oxalic, malonic, succinic, maleic, fumaric, malic, tartaric, citric, mandelic, methanesulfonic, p-toluenesulfonic, cyclamic, salicylic, aspartic, stearic or even palmitic acids.

Among the pharmaceutically acceptable bases, mention may be made in a non-limiting way, of inorganic bases for example forming ammonium salts or salts of alkaline or earth alkaline metals such as lithium, sodium, potassium, magnesium or even calcium, or organic bases such as triethylamine, diisopropylamine, piperidine or further morpholine.

The compounds of the invention will preferably not represent a compound of formula (I) for which $B_1$ et $B_2$ represent a $CH_2$ group and A represents a O—$CH_2$—$CH_2$—O or O—$CH_2$—CH=CH—$CH_2$—O (i.e. an X—Y—Z group with X=Z=O and Y representing an ethylene or but-2-enylene group).

Preferably, Y does not represent a $C_2$-$C_6$ alkenylene group.

Preferably, R2 represents a hydrogen, a $C_1$-$C_6$ alkyl group, a $C_3$-$C_8$ cycloalkyl group, an aryl-($C_1$-$C_6$)-alkylene group, an optionally substituted aryl group, or a —COR3, —$CO_2$R3 or —$SO_2$R3 group, with R3 as defined above. Further preferably, R2 represents a hydrogen, an alkyl group such as methyl, an aryl-($C_1$-$C_6$)-alkylene group such as a benzyl, a —CO—(($C_1$-$C_6$)-alkyl) group such as an acetyl, or a —CO-aryl group such as a benzoyl.

Preferably, X and Z are selected independently from O, S and NR2 with R2 as defined earlier, and do not each represent advantageously an oxygen atom.

Preferably, A does not represent a —SO— or —$SO_2$— group or further a —NMe-($C_1$-$C_6$)-alkylene-NMe- group.

According to a first advantageous embodiment of the invention, the dimeric derivatives of the invention will include at least one non-oxidized sulfur atom (i.e. A represents —S—, —S—S— or —X—Y—Z— with at least X or Z representing S and/or Y representing —(CO)$_r$—(CH$_2$)$_s$—Y2-(CH$_2$)$_t$—(CO)$_u$— with Y2=S, S—S or a heteroaromatic ring containing a sulfur atom such as a thienyl) and advantageously two sulfur atoms in their group A (i.e. A represents —S—S— or —X—Y—Z— with X and Z representing S and Y being such as defined above or X or Z representing S and Y representing —(CO)$_r$—(CH$_2$)$_s$—Y2-(CH$_2$)$_t$—(CO)$_u$— with Y2=S, S—S or a heteroaromatic ring containing a sulfur atom such as a thienyl or preferably S—S or a thienyl).

Preferably, A will represent an X—Y—Z group, for which X and/or Z, advantageously X and Z, represents a sulfur atom and Y is as defined above.

According to a second advantageous embodiment of the invention, A represents an X—Y—Z group with Y representing:
 a —CO—Y1-CO— group, with Y1 as defined above, or
 a —CO—(CH$_2$)$_s$—Y2-(CH$_2$)$_t$—CO— group with s, t and Y2 as defined above.

In this particular embodiment, X and Z are preferably identical and each represent advantageously O or NR2, with R2 as defined earlier and preferably representing a hydrogen atom.

Advantageously, Y2 will not represent —SO— or —$SO_2$—. Preferably, Y2 will represent —S—, —S—S—, —Se—Se—, —NR2-, a $C_3$-$C_8$ cycloalkylene group or an optionally substituted aromatic or heteroaromatic ring. Still preferably, Y2 will represent an optionally substituted aromatic or heteroaromatic ring.

Preferably, $B_1$ and $B_2$ are identical and each represents a $CH_2$ group.

According to a third advantageous embodiment of the invention, A includes at least one heteroaromatic ring or heterocycle, the latter including at least one nitrogen ring atom.

With the presence of a nitrogen atom, an acid addition salt may be formed with the molecules of the invention in order to increase their solubility.

Thus, A will preferably represent an X—Y—Z chain with:
 X and/or Z representing a heterocycle, and/or
 Y representing a —(CO)$_r$—(CH$_2$)$_s$—Y2-(CH$_2$)$_t$—(CO)$_u$— group for which r, s, t and u are as defined above and Y2 represents an optionally substituted heteroaromatic ring.

Advantageously, the heteroaromatic ring and/or heterocycle will be selected from pyridine, pyrimidine, pyridazine, pyrazine, indole, triazole, pyrazole, imidazole, triazole, morpholine, piperazine, piperidine, pyrrolidine, tetrazole or further pyrrole. Preferably, this is a pyridine or piperazine.

According to a fourth advantageous embodiment of the invention, $B_1$ and/or $B_2$ represent a CHOH group.

Thus, base addition salts with which solubility may be increased, may be obtained with the molecules of the invention.

In particular, the dimeric derivatives of the invention may be selected from the following molecules:

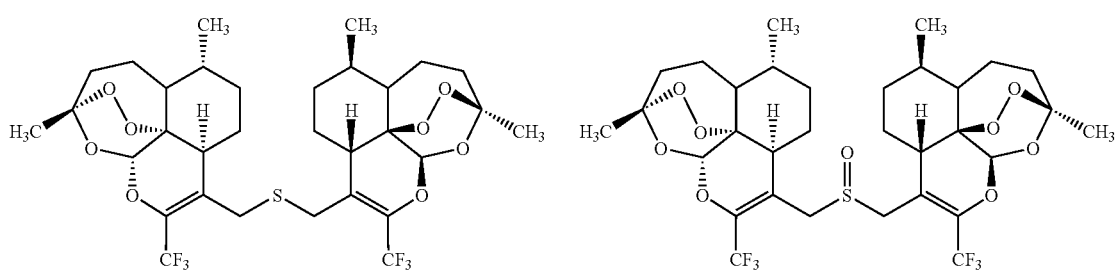

-continued
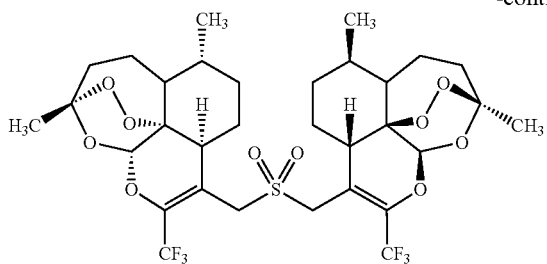
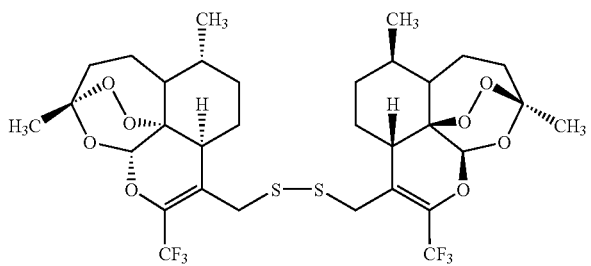
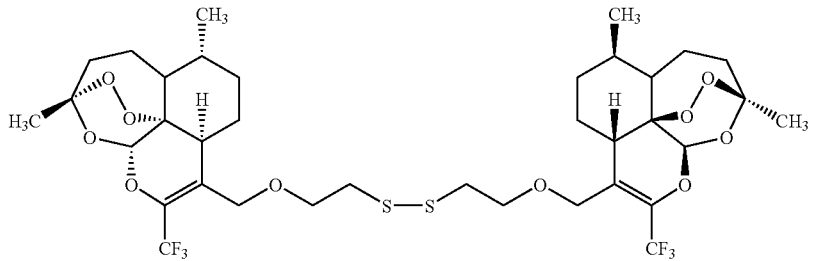
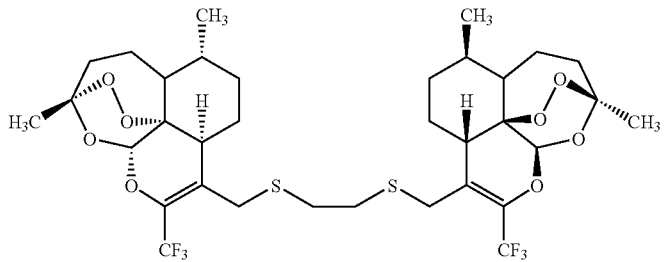
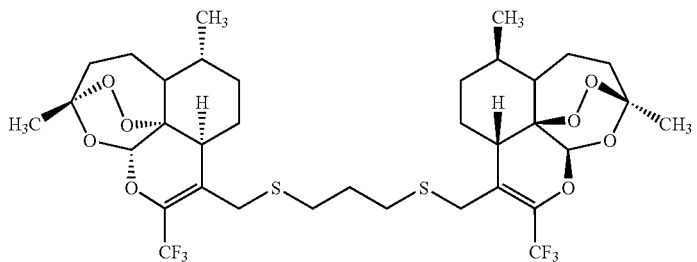
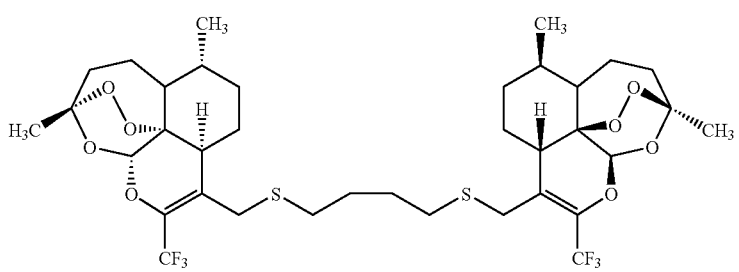

-continued
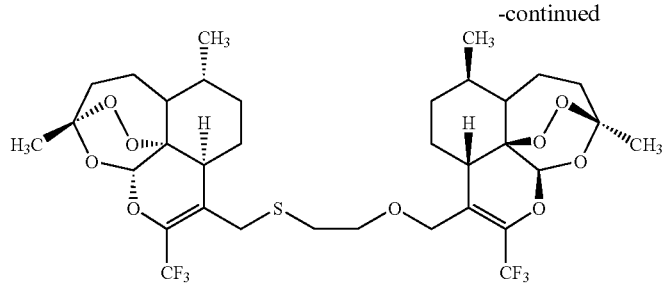
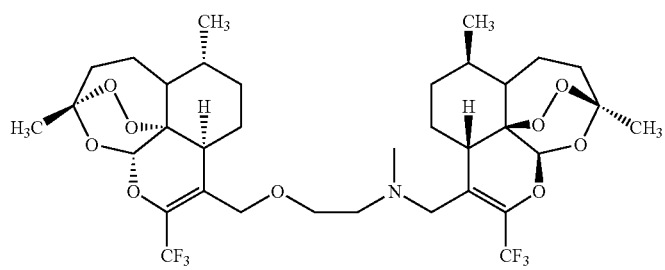
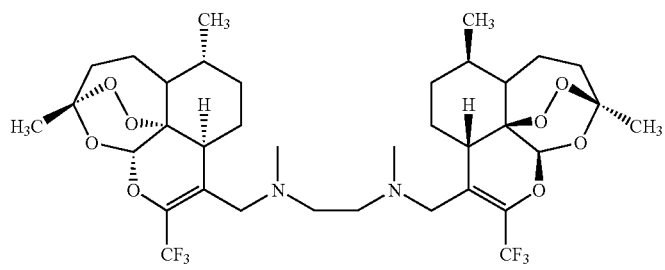
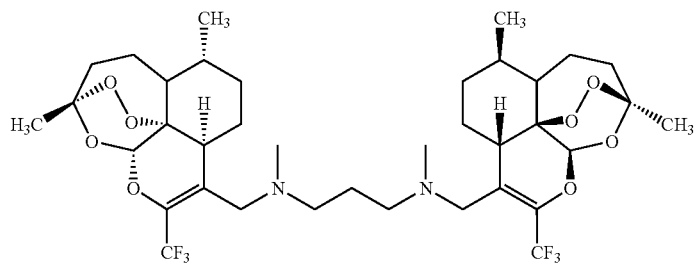
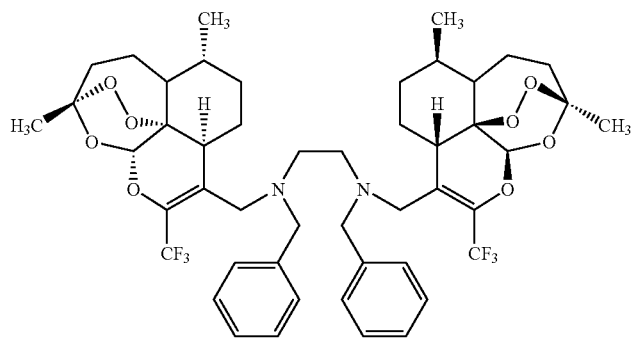
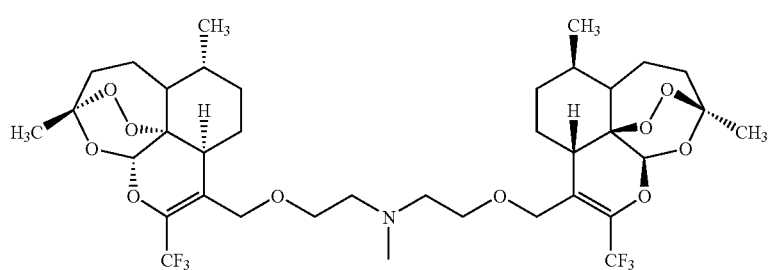

-continued
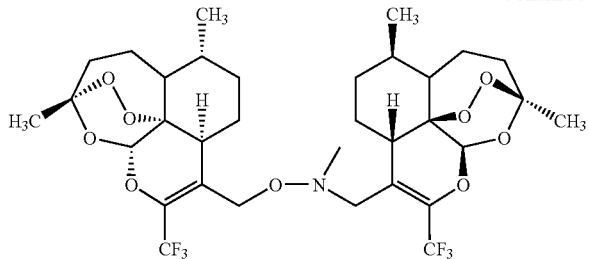
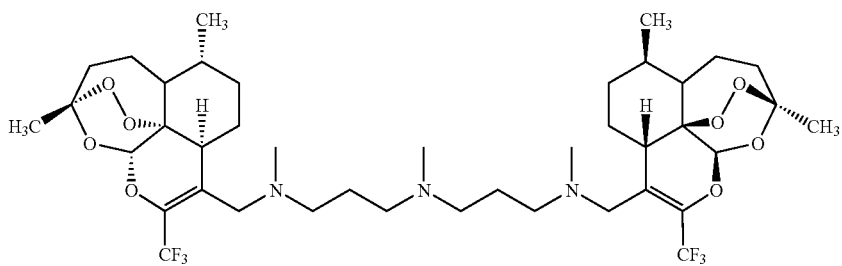
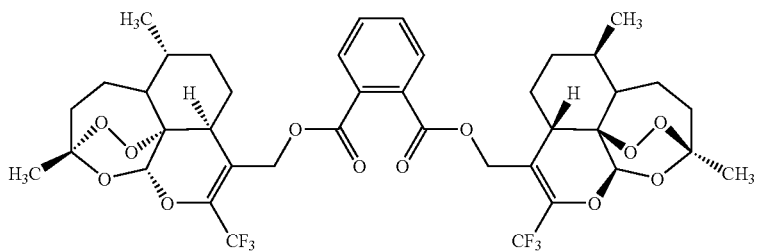
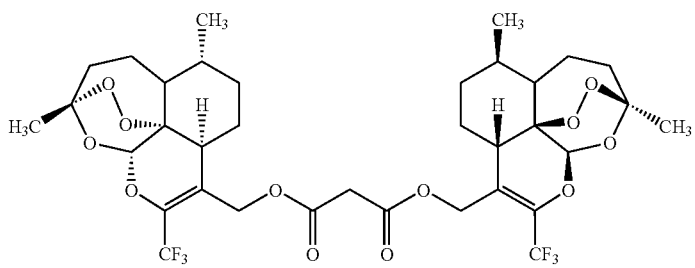
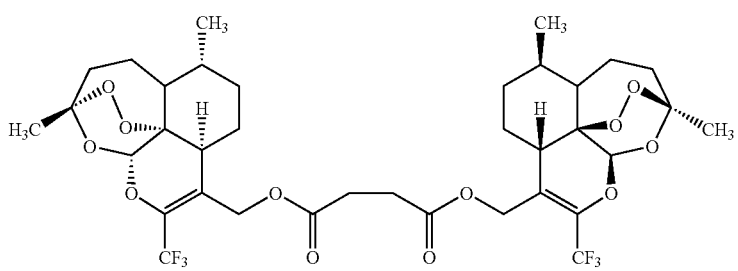
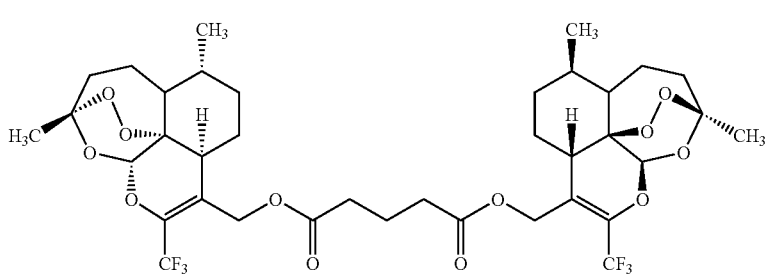

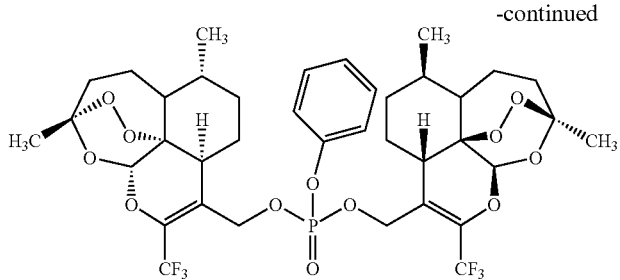
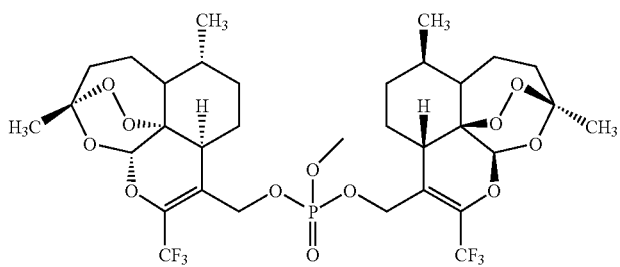
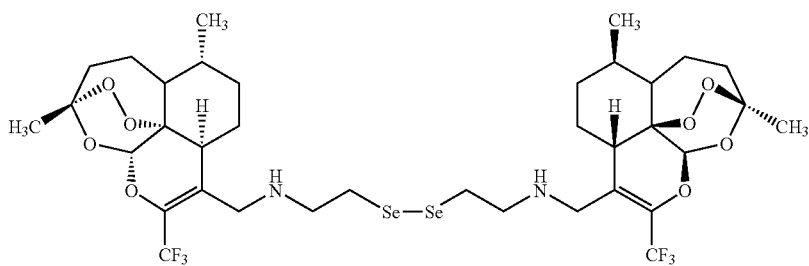
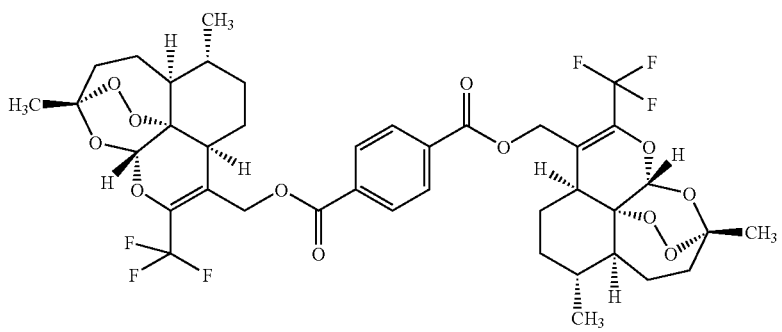
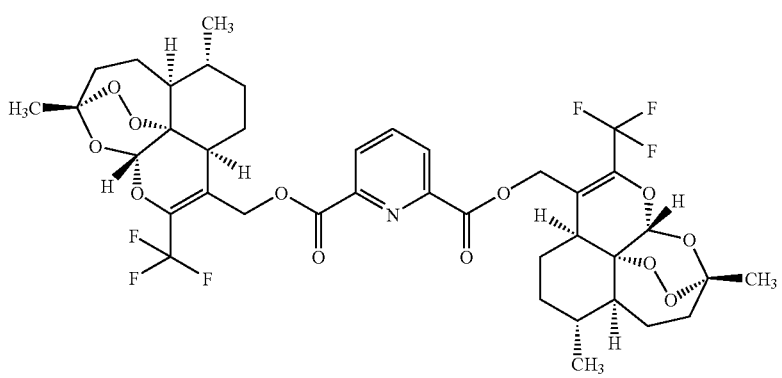

-continued
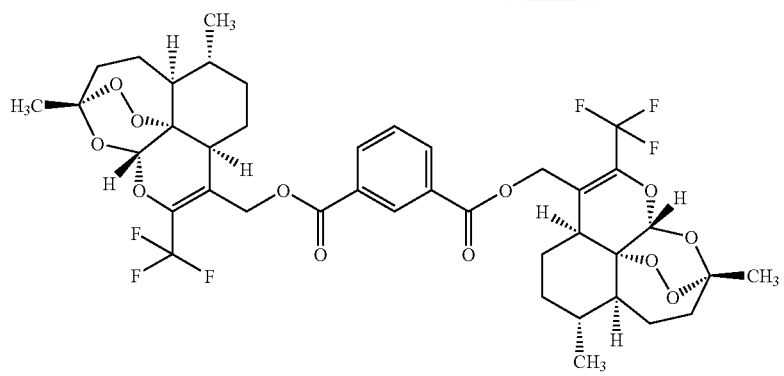
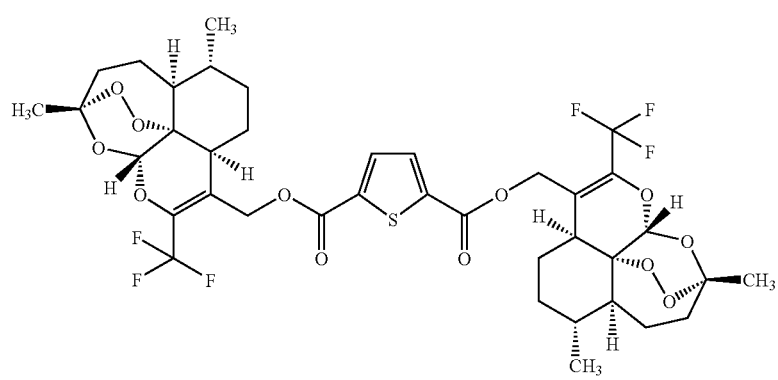
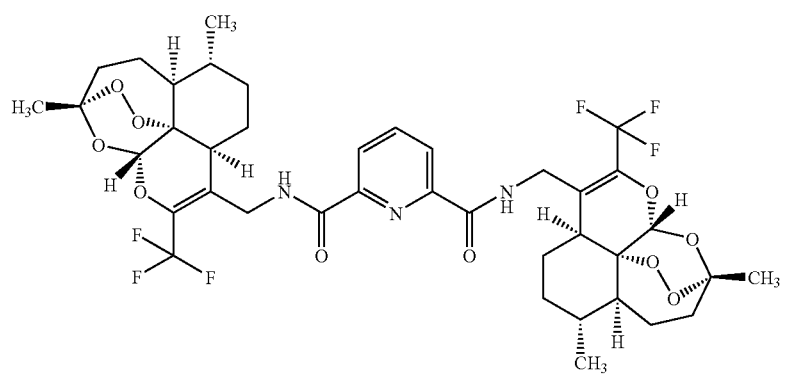
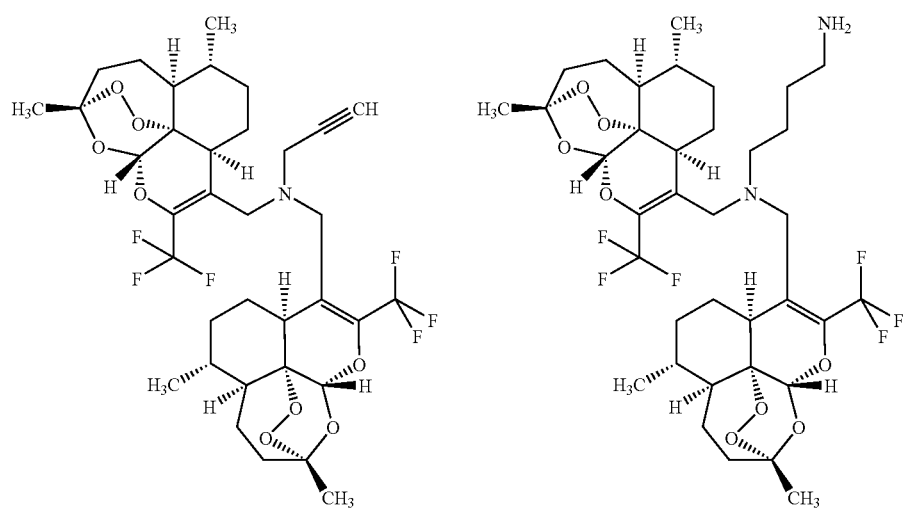

-continued
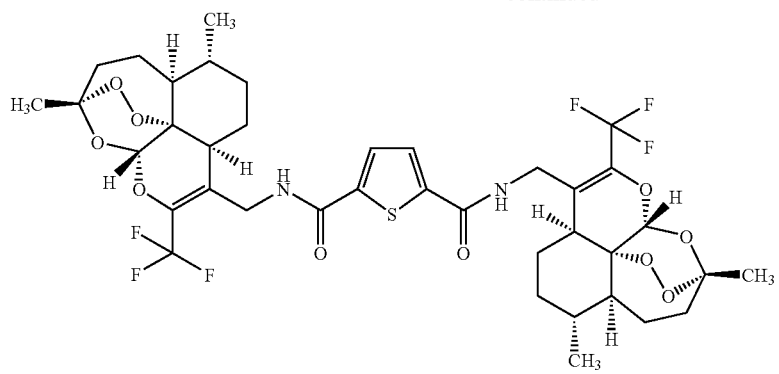
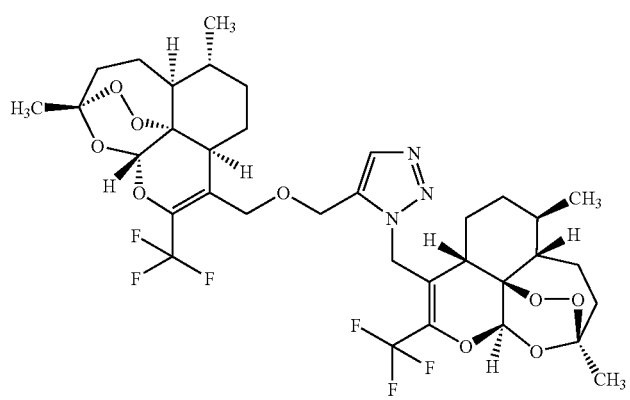
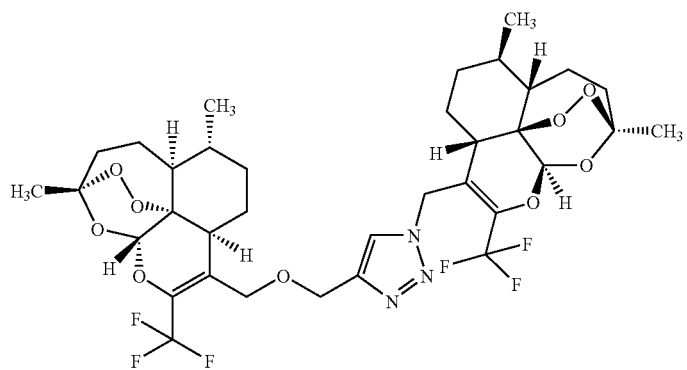
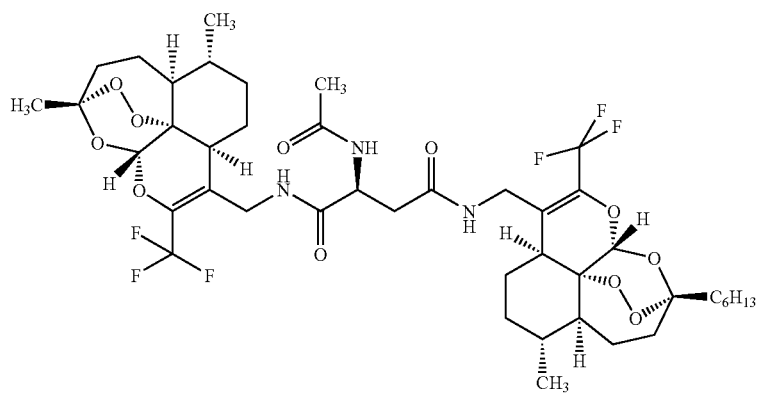

-continued
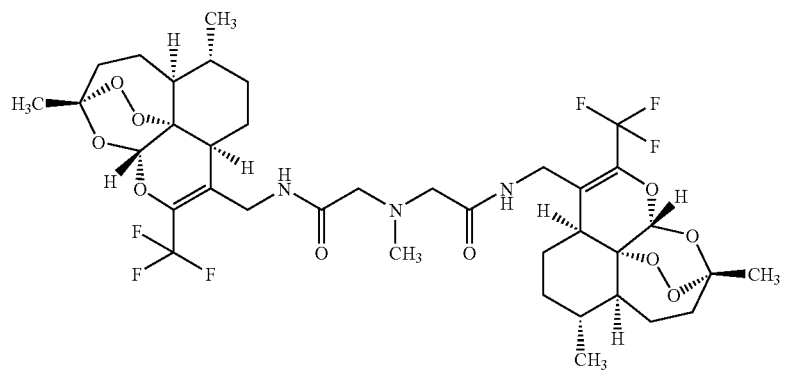
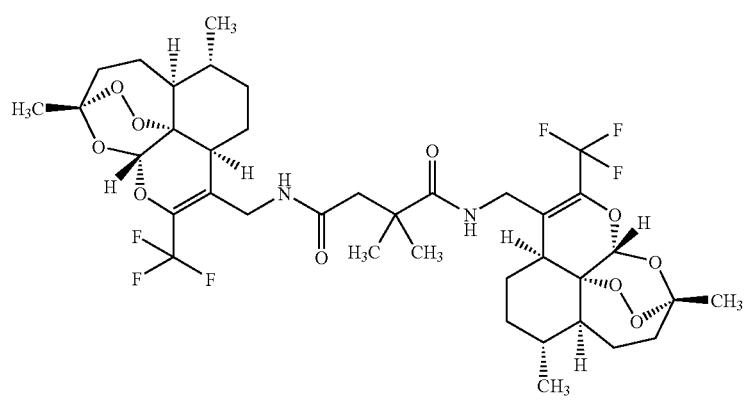
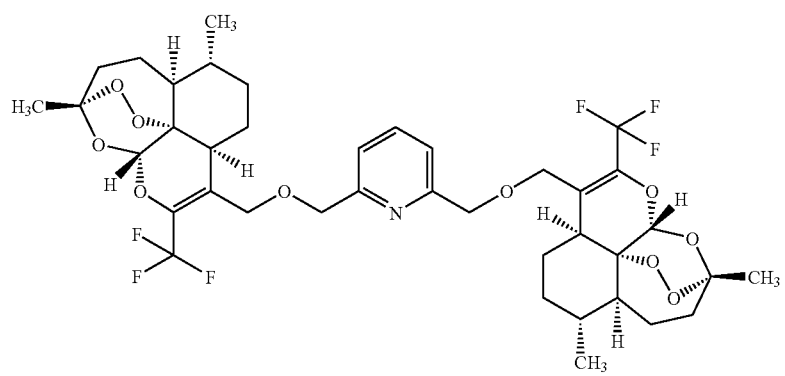
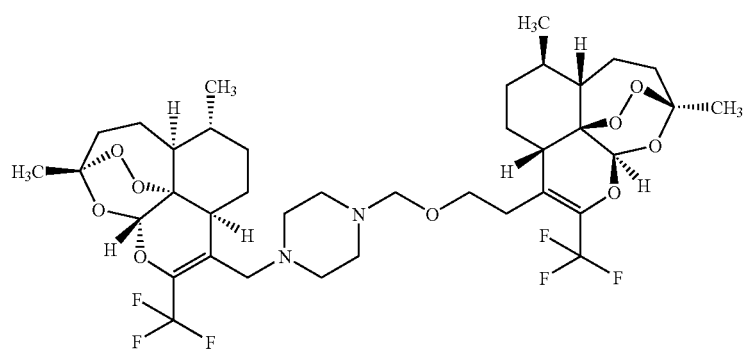

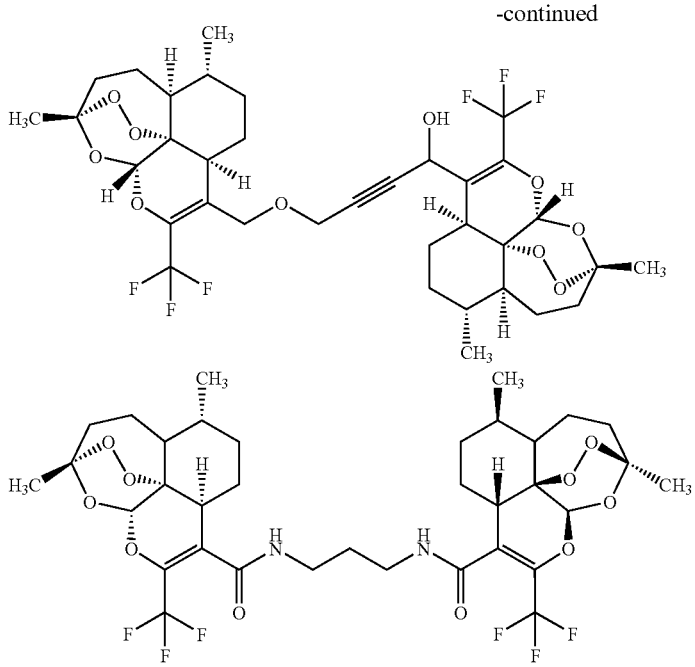

Advantageously, the dimeric derivatives of the invention may be used as a drug and in particular for treating cancer.

The object of the present invention is also the use of dimeric derivatives of 10-trifluoromethylated artemisinin as described earlier for preparing a drug, notably intended for treating cancer.

The present invention also relates to a method for treating cancer comprising the administration of an effective amount of at least one compound of formula (I) as defined above to a patient in need thereof.

The object of the present invention is also a pharmaceutical composition comprising at least one dimeric derivative of 10-trifluoromethylated artemisinin as described earlier in association with a pharmaceutically acceptable carrier.

The compounds according to the invention may be administered via an oral, sublingual, parenteral, subcutaneous, intramuscular, intravenous, transdermal, local or rectal route, and preferably via an oral, intravenous or subcutaneous route.

In the pharmaceutical compositions of the present invention for an oral, sublingual, parenteral, subcutaneous, intramuscular, intravenous, transdermal, local or rectal administration, the active ingredient may be administered as administration unit forms, mixed with standard pharmaceutical supports, to animals or to humans. The suitable administration unit forms comprise oral forms such as tablets, gelatin capsules, powders, granules, and oral solutions or suspensions, sublingual and buccal administration forms, parenteral, subcutaneous, intramuscular, intravenous, intranasal or intraocular administration forms and rectal administration forms.

When a solid composition is prepared as tablets, the main active ingredient is mixed with a pharmaceutical carrier such as gelatin, starch, lactose, magnesium stearate, talc, acacia gum, or the like. The tablets may be coated with saccharose or other suitable materials, or further they may be treated so as to have prolonged or delayed activity and to continuously release a predetermined amount of active ingredient.

A gelatin capsule preparation is obtained by mixing the active ingredient with a diluent and by pouring the obtained mixture into soft or hard gelatin capsules.

A preparation as a syrup or elixir may contain the active ingredient together with a sweetener, an antiseptic, as well as a gustatory agent and a suitable coloring agent.

The powders or granules dispersible in water may contain the active ingredient mixed with dispersants or wetting agents, or suspension agents, as well as taste-correcting agents or sweeteners.

For rectal administration, one resorts to suppositories which are prepared with binders which melt at the rectal temperature, for example cocoa butter or polyethylene glycols.

For parenteral, intranasal or intraocular administration, aqueous suspensions, isotonic saline solutions or sterile and injectable solutions are used, which contain pharmacologically compatible dispersants and/or wetting agents.

The active ingredient may also be formulated as microcapsules, optionally with one or more additive supports.

The compounds of the invention may be used at doses comprised between 0.01 mg and 1,000 mg per day, given in single dose once daily or administered in several doses all along the day, for example twice a day in equal doses. The daily administered dose is advantageously comprised between 5 mg and 500 mg, even more advantageously between 10 mg and 200 mg. It may be necessary to use doses exceeding these ranges, which one skilled in the art may himself/herself take into account.

In a particular embodiment, this composition may comprise additionally at least one other active ingredient, advantageously selected from anticancer agents.

As an anticancer agent, mention may be made in a non-limiting way of 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

The object of the present invention is also a pharmaceutical composition comprising:

(i) at least one compound of formula (I) as defined above, and (ii) at least one active ingredient, notably useful for treating cancer, as combination products for simultaneous, separate or spread out over time use.

As an active ingredient, mention may notably be made, in a non-limiting way, of 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

Pharmaceutical compositions as described above may be in particular used as a drug, notably for treating cancer.

The present invention also relates to the use of a composition as the one described above for making a drug, in particular intended for treating cancer.

The compounds of the invention may be notably prepared from the artemisinin bromo-trifluoromethylated intermediate derivative A and from the hydroxylated derivative B, the syntheses of which are described in [*J. Med. Chem.*, 47, 1423-33, (2004); WO 03/035 651].

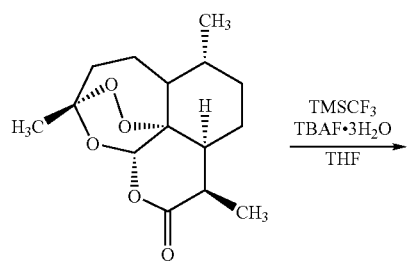

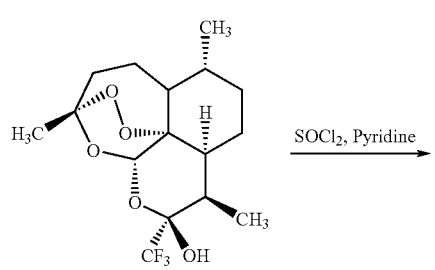

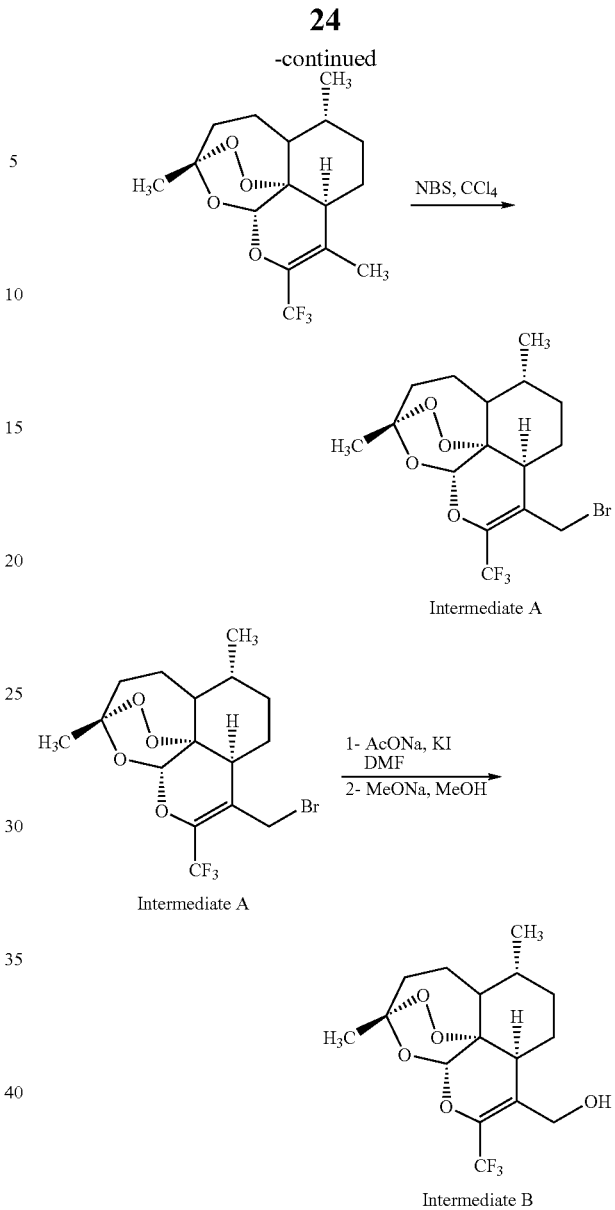

N.B.: TMS=trimethylsilyl; TBAF=tetrabutylammonium fluoride; THF=tetrahydrofurane; NBS=N-bromosuccinimide, Ac=acetyl; Me=methyl; DMF=dimethylformamide.

The intermediate monomers C and D, which may also be used as a starting product for preparing the compounds of the invention, are obtained according to the following synthesis routes:

Synthesis of the Intermediate C:

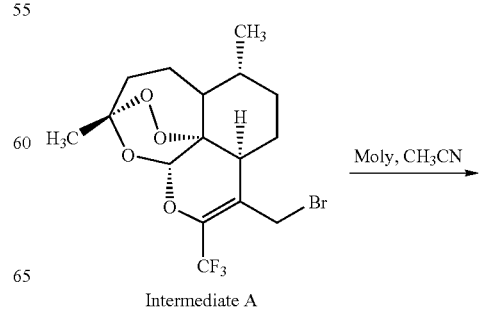

-continued

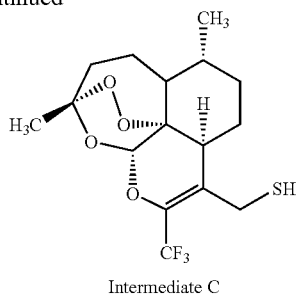

Intermediate C

To a solution of A (0.800 g, 1.94 mmol) in acetonitrile (20 mL), benzyltriethylammonium tetrathiomolybdate [(PhCH$_2$NEt$_3$)$_2$][MoS$_4$] (1.24 g, 2 mmol, 1.03 eq.) (currently called Moly, a synthesis of which is described in *Synth. Commun.*, 22, 3277-84 (1992)) is added. The reaction mixture is stirred for 45 minutes at room temperature and then 100 mL of diethyl ether are added in order to precipitate the molybdate salts. After filtration on celite, the residue is extracted with a diethyl ether/dichloromethane (5:1, 2*60 mL) mixture. The organic phases are again filtered on celite before evaporating the solvents under reduced pressure. The crude reaction product is purified by chromatography on silica gel (petroleum ether/ethyl acetate 8:2); the intermediate thiol C is isolated with a yield of 60% (0.426 g).

Synthesis of the Intermediate D:

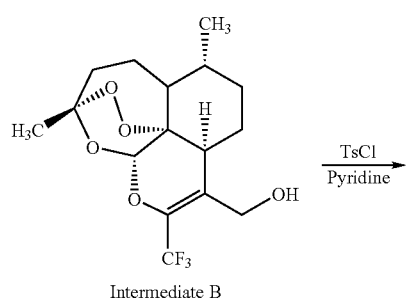

Intermediate B

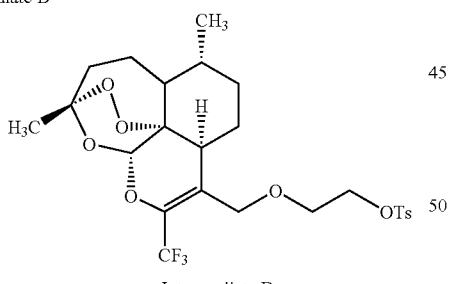

Intermediate D

To a solution in pyridine (1.4 mL) of the intermediate B (0.282 g, 0.72 mmol), tosyl chloride [TsCl] (0.206 g, 1.08 mmol, 1.5 eq.) is added at 0° C. under argon. The reaction mixture is stirred for 18 hours at room temperature. After dilution with dichloromethane (10 mL), the organic phase is washed with a 20% hydrochloric acid solution (10 mL) and then with water (10 mL) and then dried on magnesium sulphate. After filtration, the solvents are evaporated under reduced pressure. The crude reaction product is purified by chromatography on silica gel (cyclohexane/ethyl acetate 7:3); the intermediate tosylate D is isolated with a yield of 80% (colorless oil, 0.316 g).

The intermediate monomers E, F, G, H, I and J which may also be used as a starting product for preparing the compounds of the invention, are obtained from the intermediate A according to the methods described below.

Synthesis of the Intermediate E:

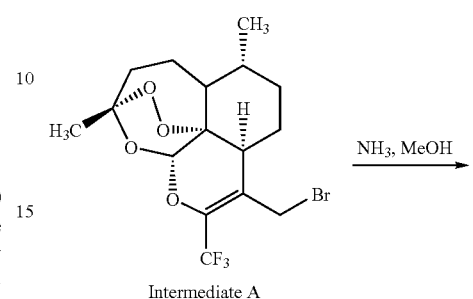

Intermediate A

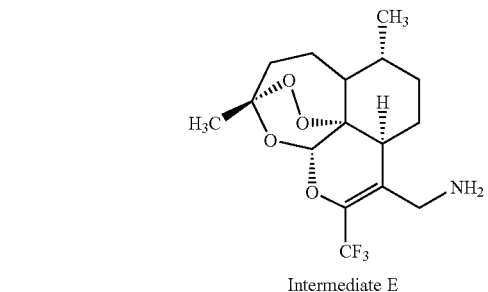

Intermediate E

The intermediate A (1.03 g, 2.5 mmol) is dissolved in an ammonia solution in methanol (7N, 10 mL). The reaction mixture is stirred at room temperature for 3 hours and then evaporated under reduced pressure. The residue is purified by chromatography on silica gel (dichloromethane/methanol 95:5 and then 90:10); the intermediate E is isolated with a yield of 59% (pale yellow powder, 0.52 g).

Synthesis of the Intermediate F:

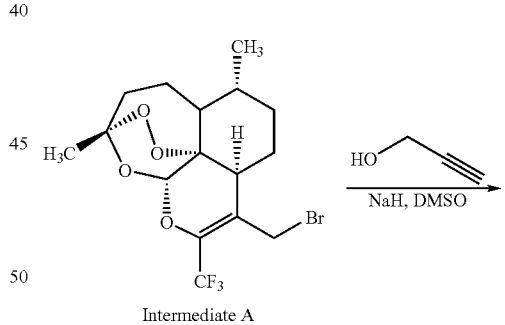

Intermediate A

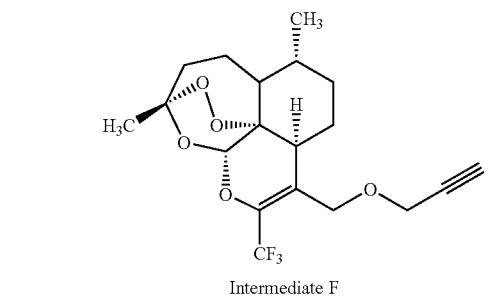

Intermediate F

To a suspension in dimethylsulfoxide (DMSO) (4 mL) of NaH (60% in oil, 0.04 g, 1.0 mmol, 1 eq.), propargyl alcohol (64 μL, 1.0 mmol, 1 eq.) is added; after 5 minutes of stirring, a solution of the intermediate A (0.41 g, 1.0 mmol) in dimethylsulfoxide (2 mL) is added to this mixture. The reaction medium is stirred at room temperature for 1.5 hours before dilution with ethyl acetate. The organic phase is washed with a sodium hydrogencarbonate solution and then dried on magnesium sulphate. After filtration, the solvents are evaporated under reduced pressure. The obtained crude product is purified by chromatography on silica gel (cyclohexane/ethyl acetate 95:5); the intermediate F is isolated with a yield of 80% (colorless oil, 0.31 g).

Synthesis of the Intermediate G:

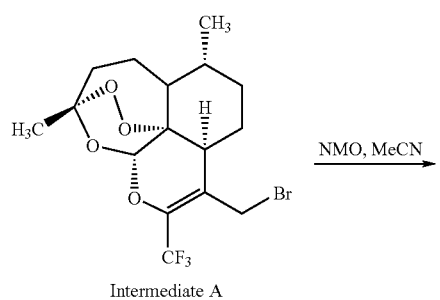

Intermediate A

To a solution of A (0.83 g, 2.0 mmol) in acetonitrile (20 mL), N-methyl-morpholine oxide (NMO) (1.08 g, 8.0 mmol, 4 eq.) is added. The reaction mixture is stirred for 1 hour at room temperature and then condensed under reduced pressure. The residue is taken up in dichloromethane and washed with water. The organic phase is then dried on magnesium sulfate, filtered and evaporated under reduced pressure. The thereby obtained intermediate aldehyde G (white powder, 0.68 g, 98%) is directly engaged into the following reactions without any additional purification step.

Synthesis of the Intermediate H:

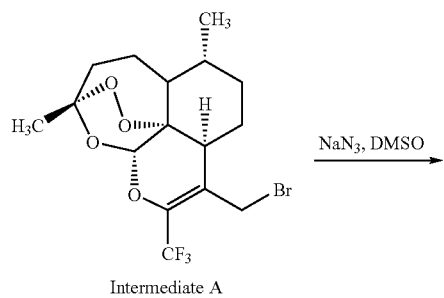

Intermediate A

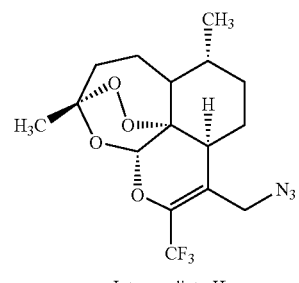

Intermediate H

To a solution of the intermediate A (0.07 g, 0.15 mmol) in dimethylsulfoxide (2 mL), sodium nitride (0.02 g, 0.3 mmol, 2 eq.) is added. The reaction mixture is stirred at room temperature for 1 hour. After dilution with ethyl acetate, the organic phase is washed with water and dried on magnesium sulphate. After filtration, the solvents are evaporated under reduced pressure and the intermediate H obtained quantitatively (white powder) is directly engaged into the next step without any additional purification.

Synthesis of the Intermediate I:

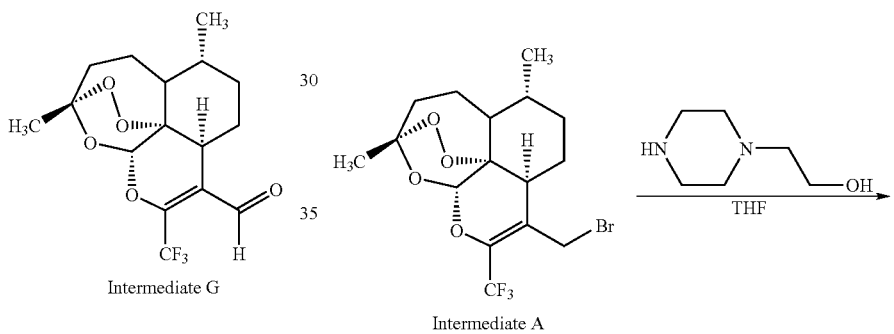

Intermediate A

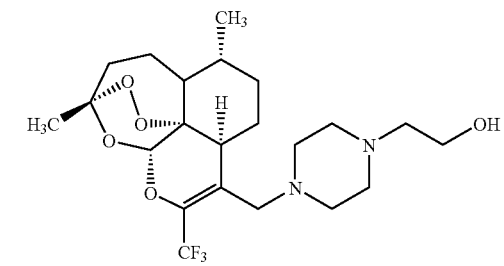

Intermediate I

To a solution of the intermediate A (1 g, 2.4 mmol) in tetrahydrofurane (15 mL), N-(2-hydroxyethyl)piperazine (1.19 mL, 9.7 mmol, 4 eq.) is added at 0° C. The reaction medium is stirred at 0° C. for 4 hours. After adding water, the mixture is extracted with diethyl ether. The organic phase is washed with a saturated sodium chloride solution and then dried on magnesium sulphate. After filtration, the solvents are evaporated under reduced pressure. The obtained crude product is purified by chromatography on silica gel (dichloromethane/methanol 97:3 to 94:6); the intermediate I is isolated with a yield of 84% (yellow powder, 0.92 g).

Synthesis of the Intermediate J:

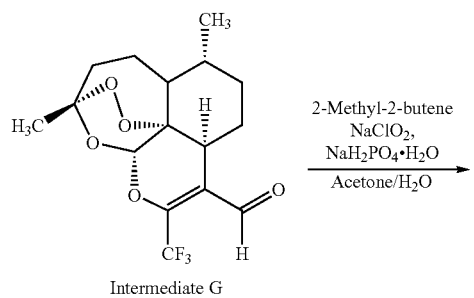

Intermediate G

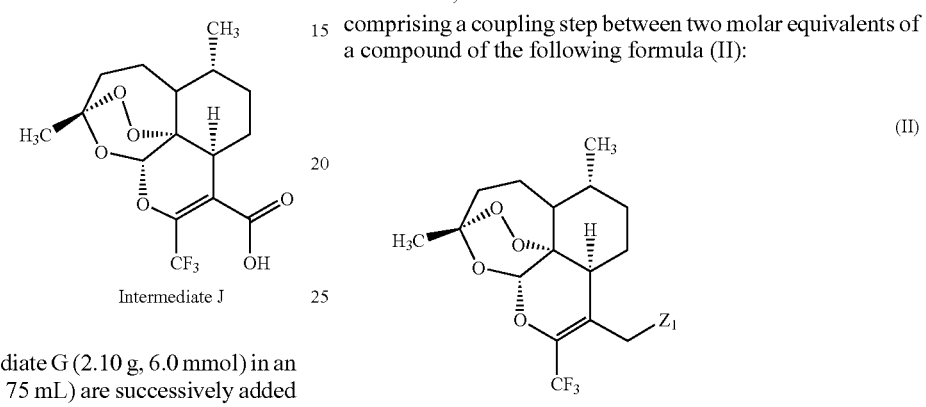

Intermediate J

To a solution of the intermediate G (2.10 g, 6.0 mmol) in an acetone/water mixture (1.5/1, 75 mL) are successively added 2-methyl-2-butene (3.2 mL, 30.1 mmol, 5 eq.), sodium phosphate monohydrate (2.50 g, 18.1 mmol, 3 eq.) and then sodium chlorite (1.64 g, 18.1 mmol, 3 eq.). The reaction mixture is stirred for 18 hours at room temperature and then condensed under reduced pressure. After dilution with ethyl acetate, the organic phase is washed with water and then with a saturated sodium chloride solution and dried on magnesium sulphate. After filtration, the solvents are evaporated under reduced pressure. The residue is purified by chromatography on silica gel (cyclohexane/ethyl acetate 80:20); the intermediate J is isolated with a yield of 54% (white powder, 1.2 g).

Thus, the compounds of the invention may notably be prepared from the intermediates A, B, C, D, E, F, G, H, I and/or J by a coupling reaction. This coupling reaction will generally comprise a single step, notably when the synthesized molecule is symmetrical (two molar equivalents of intermediate being used), but may comprise several reaction steps, two different intermediates being able to be used in the case of non-symmetrical molecules. These reaction coupling steps are carried out with techniques well-known to one skilled in the art.

The compound of formula (I), thereby obtained by coupling, may be separated from the reaction medium with methods well-known to one skilled in the art, such as for example by extraction, evaporation of the solvent or further by precipitation and filtration.

The compound may moreover be purified if need be by techniques well-known to one skilled in the art, such as by crystallization if the compound is crystalline, by distillation, by chromatography on a silica gel column or further by high performance liquid chromatography (HPLC).

The groups $B_1$ and/or $B_2$ representing a $CH_2$ in the compounds of the invention will more particularly be obtained from the intermediates A-F, H or I.

Also, the groups $B_1$ and/or $B_2$ representing a CHOH group in the compounds of the invention will more particularly be obtained from the intermediate G, by adding a suitable anion on the aldehyde function of the intermediate G.

Finally, the groups $B_1$ and/or $B_2$ representing a C=O group in the compounds of the invention will more particularly be obtained from the intermediate J by a suitable coupling reaction, such as a peptide coupling for forming an amide function or further an esterification reaction for forming an ester function, according to techniques well-known to one skilled in the art.

An object of the present invention is therefore also, according to a first particular embodiment, a method for preparing a compound of formula (I) as defined earlier for which:

$B_1$ and $B_2$ each represent a $CH_2$ group, and

A represents an X—Y—Z group with X, Y and Z as defined earlier, comprising a coupling step between two molar equivalents of a compound of the following formula (II):

(II)

for which $Z_1$ represents a halogen atom and preferably a bromine atom, and at least one molar equivalent of a compound of the following formula (III):

$$Z_2—Y—Z_3 \quad (III),$$

for which $Z_2$ and $Z_3$ represent, independently of each other, an OH, SH or NHR2 group or a heterocycle including a NH group, Y and R2 being as defined above.

By "at least one molar equivalent", is meant in the sense of the present invention, that at least one mole of the compound (III) for two moles of the compound (II) is used in the coupling reaction. Advantageously, 1 to 1.5, preferably about 1, molar equivalent of the compound (III) will be used.

This coupling reaction will be advantageously carried out in a basic medium, notably in the presence of NaH or $K_2CO_3$, preferably at room temperature. A solvent such as dimethylsulfoxide or acetonitrile may be used.

Preferably, Y will not represent a —CO—Y1-CO— or —CO—$(CH_2)_s$—Y2-$(CH_2)_t$—CO— group.

Advantageously, X and Z represent independently of each other, O, S or NR2 with R2 such as defined earlier. In this case, $Z_2$ and $Z_3$ will represent independently of each other, an OH, SH or NHR2 group.

The object of the present invention according to a second particular embodiment is also a method for preparing a compound of formula (I) as defined above for which:

$B_1$ and $B_2$ each represent a $CH_2$ group, and

A represents an X—Y—Z group for which:

X and Z are identical and are selected from O, S and NR2, with R2 as defined above, and Y is as defined earlier, comprising a coupling step between two molar equivalents of a compound of the following formula (IV):

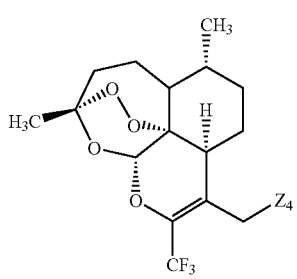

(IV)

for which $Z_4$ represents an OH, SH or NHR2 group, with R2 as defined above,
and at least one molar equivalent of a compound of the following formula (V):

$$Z_5—Y—Z_6 \quad (V),$$

for which $Z_5$ and $Z_6$ represent independently of each other, a halogen atom such as a chlorine or a bromine, and preferably a chlorine, and Y is as defined above.

Also by "at least one molar equivalent", is notably meant from 1 to 1.5, preferably about 1, molar equivalent of the compound (V).

This coupling reaction may be carried out in dichloromethane or dimethylsulfoxide (DMSO) as a solvent, notably in the presence of 4-dimethylaminopyridine or of a base such as NaH.

The object of the present invention according to a third particular embodiment, is also a method for preparing a compound of formula (I) as defined above, for which:
  $B_1$ and $B_2$ each represent a $CH_2$ group, and
  A represents an X—Y—Z group for which:
    X and Z are identical and are selected from O, S and NR2, with R2 as defined above, and
    Y represents —CO—Y1-CO— or —CO—$(CH_2)_s$—Y2-$(CH_2)_t$—CO—, with Y1, Y2, s and t as defined above,
comprising a coupling step between two molar equivalents of a compound of the following formula (IV):

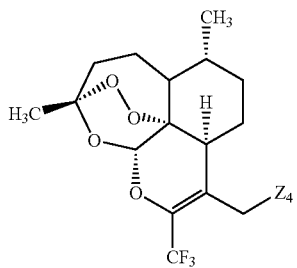

(IV)

for which $Z_4$ represents an OH, SH or NHR2 group, with R2 as defined above,
and at least one molar equivalent of a compound of the following formula (VI):

$$HO—Y—OH \quad (VI),$$

for which Y is as defined above.

Also, by "at least one molar equivalent", is notably meant 1 to 1.5, preferably about 1, molar equivalent of the compound (VI).

This coupling reaction will be achieved preferably in the presence of a coupling agent such as diisopropyl carbodiimide (DIC), dicyclohexyl carbodiimide (DCC), 1-(3-dimethylaminopropyl)-3-ethylcarbodiimide hydrochloride (EDCI), carbonyldiimidazole (CDI), 2-(H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU) or further O-(7-azobenzotriazol-1-yl)-1,1,3,3-tetramethyluronium hexafluorophosphate (HATU), optionally associated with a auxiliary coupling agent such as N-hydroxysuccinimide (NHS), N-hydroxybenzotriazole (HOBt), 3,4-dihydro-3-hydroxy-4-oxo-1,2,3-benzotriazole (HOOBt), 1-hydroxy-7-azabenzotriazole (HAt) or N-hydroxysulfosuccinimide (sulfo NHS). Advantageously, the pair EDCI/HOBt will be used.

The reaction may be conducted in dichloromethane as a solvent, notably at room temperature.

The object of the present invention is also, according to a fourth particular embodiment, a method for preparing a compound of formula (I) as defined earlier for which:
  $B_1$ and $B_2$ each represent a C=O group, and
  A represents an X—Y—Z group with X, Y and Z such as defined earlier,
comprising a coupling step between two molar equivalents of a compound of the following formula (VII):

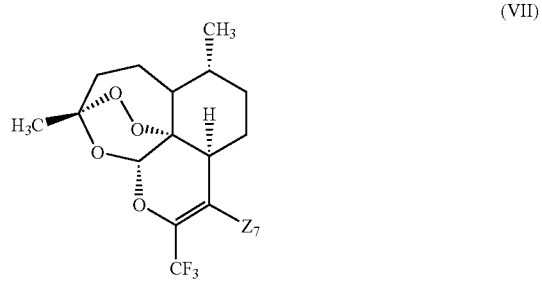

(VII)

for which $Z_7$ represents a $CO_2H$ group, optionally in an activated form,
and at least one molar equivalent of a compound of the following formula (III):

$$Z_2—Y—Z_3 \quad (III),$$

for which $Z_2$ and $Z_3$ represent independently of each other, an OH, SH or NHR2 group or a heterocycle including an NH group, Y and R2 being as defined above.

By "activated form", is meant in the sense of the present invention, a carboxylic acid function modified so as to make it more active with regards to nucleophilic groups. These activated forms are well-known to one skilled in the art and may in particular be an acid chloride (i.e. $Z_7$=COCl).

Also, by "at least one molar equivalent", is notably meant 1 to 1.5, preferably about 1, molar equivalent of the compound (III).

When the coupling reaction is conducted starting with the compound (VII) with $Z_7$=$CO_2H$ (thereby corresponding to the intermediate J), the reaction will then advantageously be conducted in the presence of a coupling agent, optionally in association with an auxiliary coupling agent as defined above, and in particular in the presence of the EDCI/HOBt pair. This reaction may be conducted at room temperature, notably in a solvent such as dichloromethane.

When the coupling reaction is conducted starting with the activated form of the carboxylic acid of the compound (VII), such as an acid chloride ($Z_7$=COCl), the reaction may then be conducted in the presence of a base.

Preferably, Y will not represent a —CO—Y1-CO— or —CO—(CH$_2$)$_s$—Y2-(CH$_2$)$_t$—CO— group.

Advantageously, X and Z will represent independently of each other, O, S or NR2 with R2 as defined earlier. In this case, Z$_2$ and Z$_3$ will represent independently of each other an OH, SH or NHR2 group.

Examples of dimeric derivatives of 10-trifluoromethylated artemisinin according to the invention were synthesized according to the procedures detailed below. These examples are only used for illustrating the invention and not for limiting the scope thereof.

Synthesis of compound 1

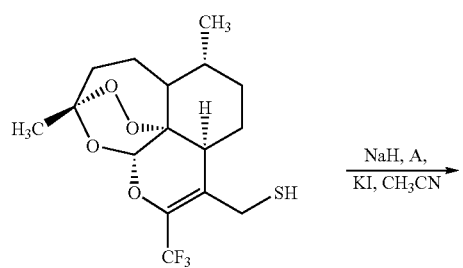

Intermediate C

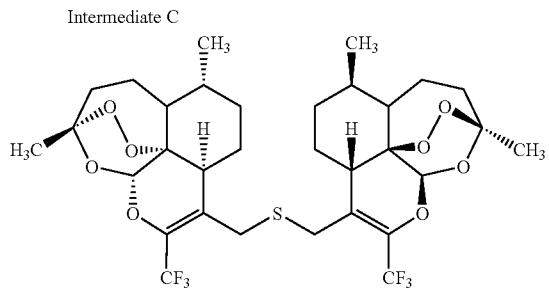

Example 1

To a suspension in dichloromethane (1 mL) of NaH (60% in oil, 0.033 g, 0.83 mmol, 1.6 eq.) at −78° C. is added a thiol C solution (0.189 g, 0.52 mmol) in dichloromethane (1 mL). After 30 minutes of stirring at −78° C., a solution of brominated derivative A (0.256 g, 0.62 mmol, 1.2 eq.) and of potassium iodide (0.1 eq.) in dichloromethane is added. The reaction mixture is stirred for 1 hour at −78° C. and then for 1 hour at room temperature before dilution with dichloromethane. The organic phase is washed with a saturated sodium chloride solution and then dried on magnesium sulphate. After filtration, the solvents are evaporated under reduced pressure. The obtained yellow solid is purified by chromatography on silica gel (petroleum ether/ethyl acetate 9:1); the product 1 is obtained as a white powder (0.301 g, 83%).

Synthesis of compound 2

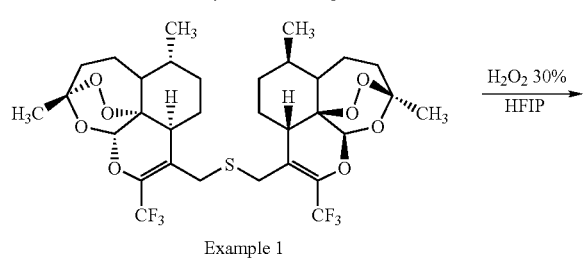

Example 1

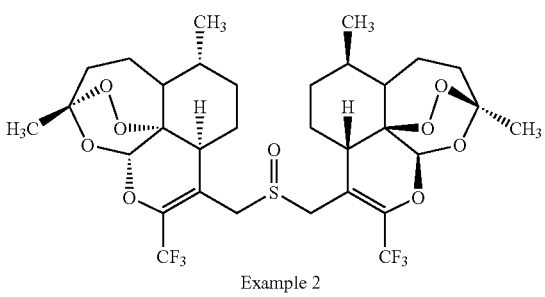

Example 2

To a solution of 1 (0.128 g, 0.18 mmol) in hexafluoroisopropanol (1.3 mL) [HFIP], H$_2$O$_2$ at 30% (42 μL, 0.36 mmol, 2 eq.) is added. After stirring at room temperature for 1 hour, the reaction medium is poured into a saturated Na$_2$SO$_3$ solution and extracted with ethyl acetate. The organic phase is washed with water and then dried on magnesium sulphate. After filtration, the solvents are evaporated under reduced pressure. The obtained yellow oil is purified by chromatography on silica gel (cyclohexane/ethyl acetate1:1); the product 2 is obtained as a mixture 1:1 of two non-separable diastereoisomers (white solid, 0.109 g, 85%).

Synthesis of compound 3

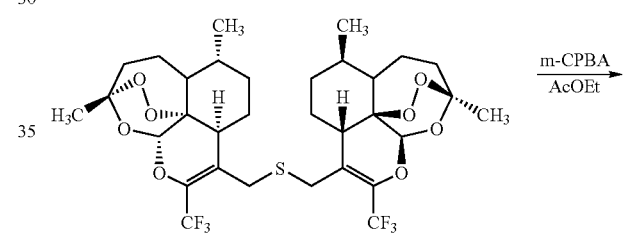

Example 1

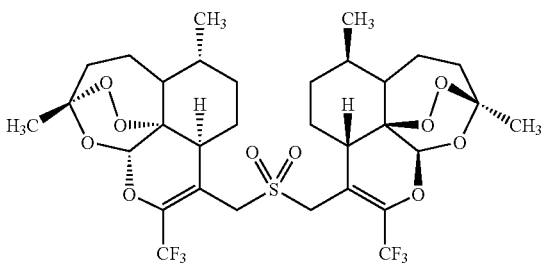

Example 3

To a solution of 1 (0.140 g, 0.2 mmol) in ethyl acetate (2 mL), m-chloroperbenzoic acid [m-CPBA] (0.087 g, 0.5 mmol, 2.5 eq.) is added and then stirring is maintained at room temperature for 3 hours. After dilution with ethyl acetate, the reaction medium is filtered on alumina. The solvents are evaporated under reduced pressure. The obtained white solid is purified by chromatography on silica gel (cyclohexane/ethyl acetate 6:4); the product 3 is isolated with a yield of 85% (white powder, 0.124 g).

Synthesis of compound 4

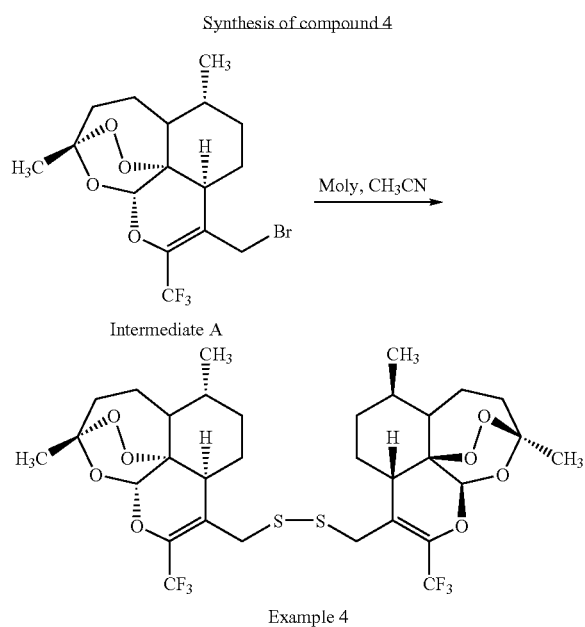

Example 4

To a solution of A (0.100 g, 0.24 mmol) in acetonitrile (2.5 mL) is added Moly (0.177 g, 0.3 mmol, 1.25 eq.). The reaction mixture is stirred for 20 hours at room temperature and then 12.5 mL of diethyl ether are added in order to precipitate the molybdate salts. After filtration on celite, the residue is extracted with a diethyl ether/dichloromethane (5:1, 4*12 mL) mixture. The organic phases are again filtered on celite after evaporation of the solvents under reduced pressure. The crude reaction product is purified by chromatography on silica gel (petroleum ether/ethyl acetate 8:2); the expected product 4 is isolated with a yield of 85% (white powder, 0.149 g).

To a solution of D (0.310 g, 0.56 mmol) in acetonitrile (3 mL) is added Moly (0.413 g, 0.68 mmol, 1.2 eq.). The reaction mixture is stirred at 24 hours at room temperature and then 40 mL of diethyl ether are added to precipitate the molybdate salts. After filtration on celite, the residue is extracted with a diethyl ether/dichloromethane (5:1, 3*30 mL) mixture. The organic phases are again filtered on celite before evaporating the solvents under reduced pressure. The crude reaction product is purified by chromatography on silica gel (petroleum ether/ethyl acetate 95:5 (100 mL), 90:10 (100 mL), 80:20 (100 mL), 70:30 (100 mL)); the expected product 5 is isolated with a yield of 65% (colorless oil, 0.298 g).

Synthesis of Compounds 6, 7, 8, 9, 10, 14 & 15

General Method A: To a suspension in dimethyl sulfoxide (c=0.25) of NaH (60% in oil, 1 eq.) is added a solution of linker (0.5 eq.) in dimethyl sulfoxide (c=0.5). After 30 minutes of stirring at room temperature, the brominated derivative A (1 eq.) and potassium iodide (0.1 eq.) are added. The reaction mixture is stirred at room temperature (for 0.5 to 3 hours) before diluting with ethyl acetate. The organic phase is washed with a saturated sodium chloride solution and then dried on magnesium sulphate. After filtration, the solvents are evaporated under reduced pressure. The obtained crude product is purified by chromatography on silica gel (cyclohexane/ethyl acetate 90:10).

Example 6: obtained with a yield of 34%, as a white powder according to the general method A, from 1,2-ethanedithiol as a linker.

Example 7: obtained with a yield of 48%, as a white powder according to the general method A, from 1,3-propanedithiol as a linker.

Example 8: obtained with a yield of 34%, as a white powder according to the general method A, from 1,4-butanedithiol as a linker.

Synthesis of compound 5

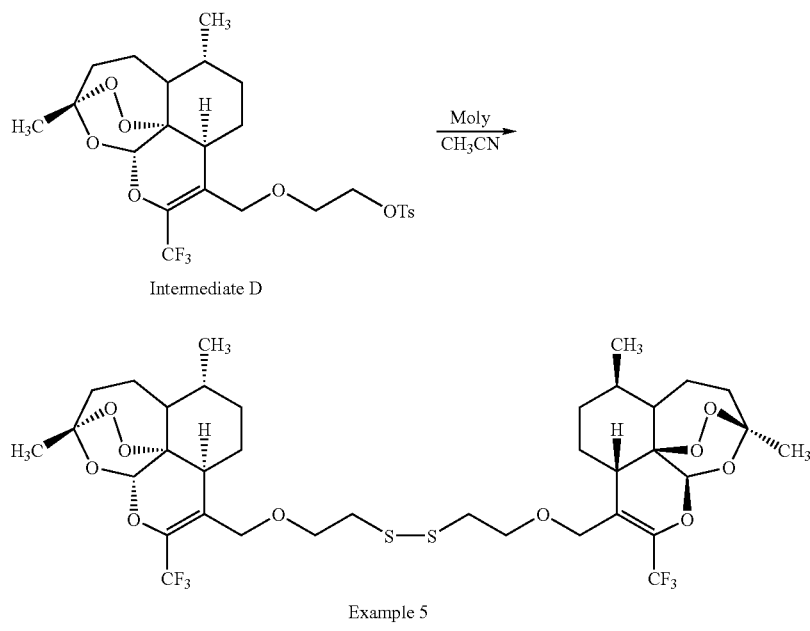

Example 5

Example 9: obtained with a yield of 12%, as a white powder according to the general method A, from 2-mercaptoethanol as a linker.

Example 10: obtained according to general method A from 2-(methylamino)ethanol as a linker.

Example 14: obtained according to general method A from N-methyldiethanolamine as a linker.

Example 15: obtained according to general method A from N-methylhydroxylamine as a linker.

Synthesis of Compounds 11, 12, 13, 16 & 23

General Method B: To a suspension in acetonitrile (c=1) of $K_2CO_3$ (0.5 eq.) is added the diamine linker (0.5 eq.). After 5 minutes of stirring at room temperature, the brominated derivative A (1 eq.) is added. The reaction mixture is stirred at room temperature (for 18-48 hours) before diluting with dichloromethane. The organic phase is washed with a saturated sodium hydrogencarbonate solution and then dried on magnesium sulphate. After filtration, the solvents are evaporated under reduced pressure. The obtained crude product is purified by chromatography on silica gel (cyclohexane/ethyl acetate 75:25).

Example 11: obtained with a yield of 85%, as a white powder according to general method B from N,N'-dimethylethylenediamine as a diamine linker.

Example 12: obtained with a yield of 36%, as a white powder according to general method B from N,N'-dimethylethyl-1,3-propanediamine as a diamine linker.

Example 13: obtained with a yield of 66%, as a white powder according to general method B from N,N'-dibenzylethylenediamine as a diamine linker.

Example 16: obtained with a yield of 10%, as a pale yellow foam according to general method B from 3,3'-bis(methylamino)-N-methyldipropylamine as a diamine linker.

Example 23: obtained according to general method B from selenocystamine dihydrochloride as a diamine linker.

Synthesis of Compounds 17, 18, 19, 20, 24, 25, 26 & 27

General Method C: To a solution in dichloromethane (c=0.04) of the intermediate B (1 eq.) is added 4-dimethylaminopyridine (1.15 eq.). The mixture is cooled to 0° C. before adding acyl bis-chloride (0.5 eq.). After returning to room temperature, the reaction mixture is stirred for 16 hours before evaporation of the solvent under reduced pressure. The obtained crude product is purified by chromatography on silica gel (cyclohexane/ethyl acetate 90:10).

Example 17: obtained with a yield of 46%, as a white powder according to general method C from ortho-phthaloyl dichloride as acyl bis-chloride.

Example 18: obtained with a yield of 28%, as white foam according to general method C from malonyl dichloride as acyl bis-chloride.

Example 19: obtained with a yield of 41%, as white foam according to general method C from ethanoyl dichloride as acyl bis-chloride.

Example 20: obtained with a yield of 40%, as yellow solid according to general method C from propanoyl dichloride as acyl bis-chloride.

Example 24: obtained with a yield of 15%, as white foam according to general method C from para-phthaloyl dichloride as acyl bis-chloride.

Example 25: obtained with a yield of 6%, as white foam according to general method C from pyridine-2,6-dicarboxylate dichloride as acyl bis-chloride.

Example 26: obtained with a yield of 38%, as pale yellow powder according to general method C from meta-phthaloyl dichloride as acyl bis-chloride.

Example 27: obtained with a yield of 36%, as pale yellow powder according to general method C from thiophene-2,5-dicarboxylate dichloride as acyl bis-chloride.

Synthesis of Compounds 21 & 22

General Method D: To a solution at 0° C. in tetrahydrofurane (c=0.045) of the intermediate B (1 eq.) is added sodium hexamethyldisilazide (2M in THF, 1 eq.). The mixture is stirred at 0° C. for 10 minutes before adding dichlorophosphate (0.5 eq.). After 1 hour at 0° C., the reaction mixture is hydrolyzed and then extracted with ethyl acetate. The organic phases are washed with a saturated sodium chloride solution, dried on magnesium sulphate, filtered and then condensed under reduced pressure. The obtained crude product is purified by chromatography on silica gel (cyclohexane/ethyl acetate, gradient: 90:10 to 80:20).

Example 21: obtained with a yield of 13%, as a white powder according to general method D from phenyl dichlorophosphate.

Example 22: obtained according to general method D from methyl dichlorophosphate.

Synthesis of Compounds 28 & 29

General Method E: To a solution of the brominated derivative A (1 éq.) in acetonitrile (c=1) is added the amino reagent (0.5 eq.) and then $K_2CO_3$ (1 eq.). The reaction mixture is stirred at room temperature (for 18 to 48 hrs) before diluting with a saturated sodium hydrogencarbonate solution and then extracting with ethyl acetate. The organic phase is washed with a saturated NaCl solution and then dried on magnesium sulphate. After filtration the solvents are evaporated under reduced pressure. The crude product is purified by chromatography on silica gel (cyclohexane:ethyl acetate 75:25).

Example 28: obtained with a yield of 69%, as a white powder according to general method E from propargylamine as an amino reagent.

Example 29: obtained with a yield of 52%, as a white powder according to general method E from tert-butyl N-(4-aminobutyl)carbamate as an amino reagent, after hydrolysis of the protective carbamate group by action of an HCl (4N) solution in dioxane for 12 hours.

Synthesis of Compounds 30 & 31

General Method F: To a solution of the intermediate E (1 eq.) in dichloromethane (c=0.04) is added triethylamine (1 eq.). After 5 minutes of stirring at room temperature, acyl bis-chloride (0.5 eq.) is added. The reaction mixture is stirred for 20 hrs before washing with water and extracting with ethyl acetate. The organic phase is decanted, dried on magnesium sulphate and then evaporated under reduced pressure. The obtained crude product is purified by chromatography on silica gel (cyclohexane/ethyl acetate 65:35).

Example 30: obtained with a yield of 60%, as a white powder according to general method F from pyridine-2,6-dicarboxylate dichloride as acyl bis-chloride.

Example 31: obtained with a yield of 38%, as a white powder according to general method F from thiophene-2,5-dicarboxylate dichloride as acyl bis-chloride.

Synthesis of Compounds 32 & 33

A mixture of the intermediate F (0.103 g, 0.25 mmol, 1 eq.) and of the intermediate H (0.094 g, 0.25 mmol, 1 eq.) is heated at 90° C. for 4 hours in a sealed tube. After returning to room temperature, the reaction medium is purified by chromatography on silica gel (cyclohexane/ethyl acetate from 90:10 to 75:25); the less polar compound 32 and the compound 33 are isolated with a global yield of 48% (white powder, 0.032 g and 0.060 g, respectively).

Synthesis of Compounds 34, 35 and 36

General Method G: To a solution of carboxylic diacid reagent (0.12 mmol, 0.5 eq.) in dichloromethane (5 mL) are added 1-(3-dimethylaminopropyl)-3-ethylcarbodiimide chlorhydrate (EDCI) (0.067 g, 0.91 mmol, 3 eq.) and hydroxybenzotriazole (HOBt) (0.047 g, 0.91 mmol, 3 eq.). After 30 minutes of stirring at room temperature, a solution of the intermediate E (0.087 g, 0.25 mmol, 1 eq.) in dichloromethane (5 mL) is added. The reaction mixture is stirred for 2 hours at room temperature. After addition of water, the mixture is extracted with dichloromethane. The organic phase is washed with a saturated sodium chloride solution and then dried on magnesium sulphate. After filtration, the solvents are evaporated under reduced pressure. The crude product is purified by chromatography on silica gel (dichloromethane/methanol 96:4).

Example 34: obtained with a yield of 38%, as a pale yellow powder according to general method G from N-acetyl aspartic acid as a carboxylic diacid reagent.

Example 35: obtained with a yield of 15%, as a pale yellow powder according to general method G from N-methylaminodiacetic acid as a carboxylic diacid reagent.

Example 36: obtained with a yield of 25%, as a pale yellow powder according to general method G from 2,2-dimethylsuccinic acid as a carboxylic diacid reagent.

Synthesis of Compound 37

To a solution of the intermediate B (0.13 g, 0.37 mmol) in DMSO (3 mL) is added 0.022 g (0.55 mmol, 2.2 eq.) of NaH (60% suspension in oil). After 10 min of stirring at room temperature, 2,6-bis(chloromethyl)pyridine (0.044 g, 0.025 mmol) is added. The reaction medium is stirred for 6 hours, and then washed with water and extracted with ethyl acetate. The organic phase is washed with a saturated sodium chloride solution and then dried on magnesium sulphate. After filtration, the solvents are evaporated under reduced pressure. Purification by chromatography on silica gel (cyclohexane/ethyl acetate 95:5). The compound 37 is isolated with a yield of 13%.

Synthesis of Compound 38

To a solution of the intermediate I (0.179 g, 0.38 mmol, 0.8 eq) in acetonitrile (1 mL) at 0° C. is added NaH (0.048 g, 1.21 mmol, 2.5 eq). After 10 min of stirring and returning to room temperature, a solution of the intermediate A (0.200 g, 0.48 mmol, 1 eq.) in acetonitrile (0.5 mL) is added. The reaction medium is stirred for 16 hours at room temperature. After adding water, the mixture is extracted with ethyl acetate. The organic phase is washed with a saturated sodium chloride solution and then dried on magnesium sulphate. After filtration, the solvents are evaporated under reduced pressure. Purification by chromatography on silica gel (dichloromethane/methanol/ammonia 97.5:2.25:0.25). The compound 38 is isolated as a pale yellow powder with a yield of 19%.

Synthesis of Compound 39

To a solution of the intermediate F (0.048 g, 0.12 mmol) in tetrahydrofurane (1 mL) at –78° C., n-butyl-lithium (n-BuLi) (1.6 M in hexane, 100 µL, 0.16 mmol, 1.3 eq.) is added dropwise. After 20 minutes of stirring at –78° C., a solution of the intermediate G (0.043 g, 0.12 mmol, 1 eq.) in tetrahydrofurane (1 mL) is added. The reaction mixture is then brought back to room temperature and stirred for 16 hours. After addition of a saturated ammonium chloride solution, the mixture is extracted with dichloromethane. The organic phase is then dried on magnesium sulphate, filtered and condensed under reduced pressure. The crude product is purified by chromatography on silica gel (cyclohexane/ethyl acetate 85:15). Le compound 39 is isolated as a white powder with a yield of 13%.

Synthesis of Compound 40

To a solution of the intermediate J (0.11 g, 0.30 mmol) in dichloromethane (5 mL) are added 1-(3-dimethylaminopropyl)-3-ethylcarbodiimide chlorhydrate (EDCI) (0.085 g, 0.45 mmol, 1.5 eq.) and 1-hydroxybenzotriazole (HOBt) (0.06 g, 0.45 mmol, 1.5 eq.). After 30 minutes of stirring at room temperature, a diamino-1,3-propane solution (0.011 g, 0.15 mmol, 0.5 eq.) in dichloromethane (1 mL) is added. The reaction mixture is stirred for 6 hours at room temperature. After addition of water, the mixture is extracted with dichloromethane. The organic phase is washed with a saturated sodium chloride solution and then dried on magnesium sulphate. After filtration, the solvents are evaporated under reduced pressure. The crude product is purified by chromatography on silica gel (dichloromethane/ethyl acetate 98:2 à 95:5); the compound 40 is isolated with a yield of 9% (whitish powder, 0.010 g).

The chemical structures of the different examples of the compounds of the invention synthesized according to the procedures described above are transferred into the following Table:

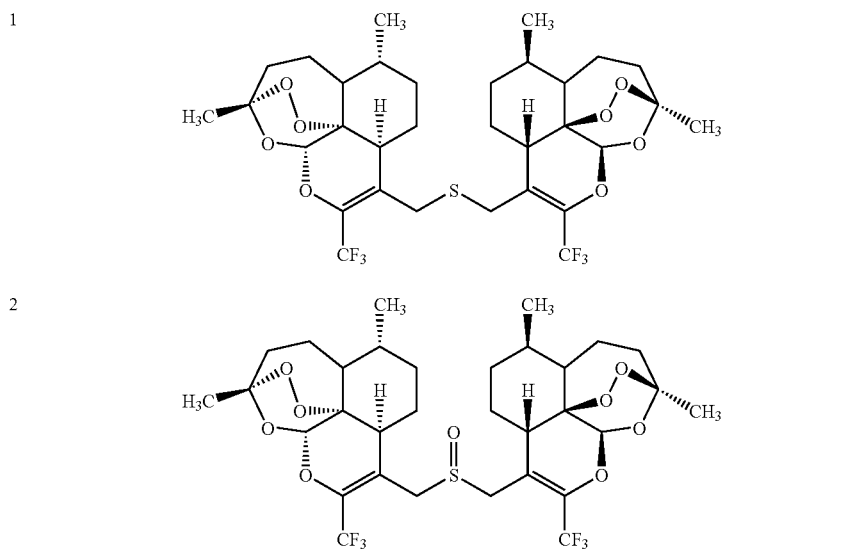

-continued
3 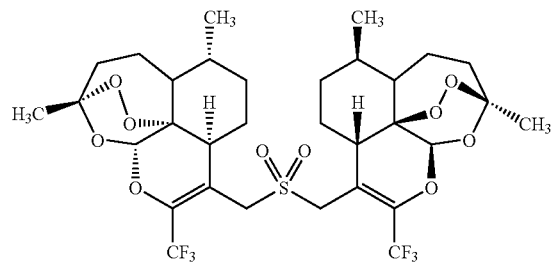
4 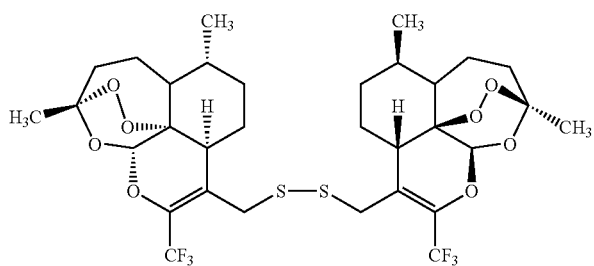
5 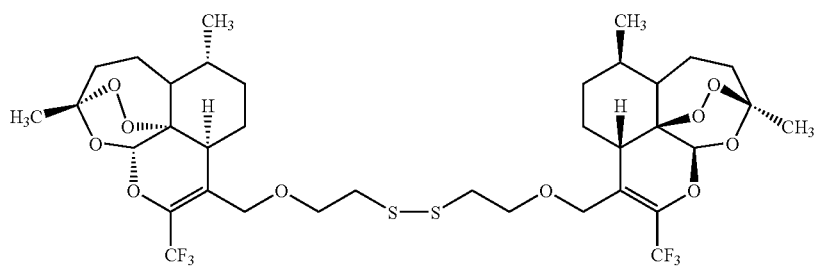
6 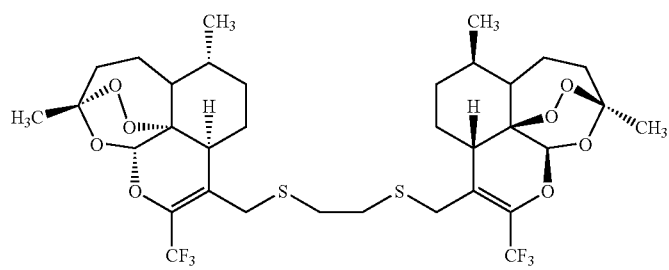
7 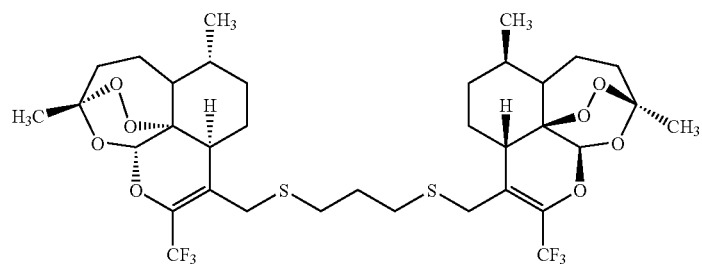
8 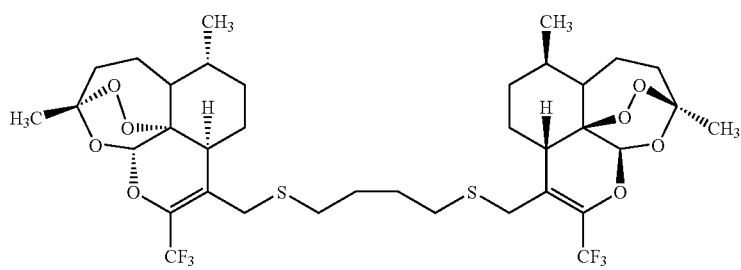

9
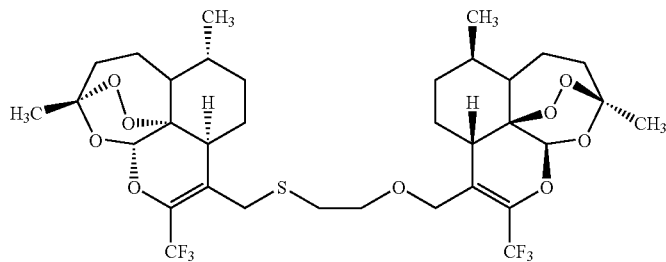
10
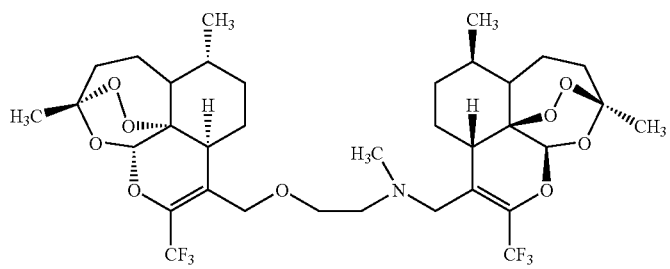
11
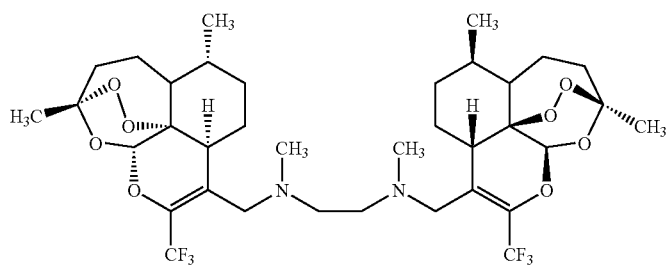
12
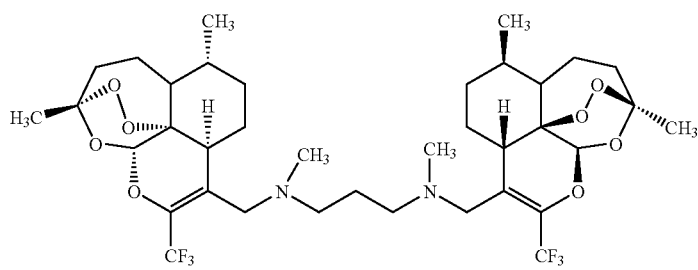
13
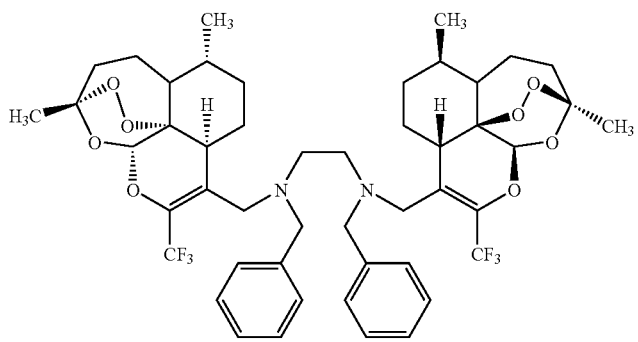

-continued
14
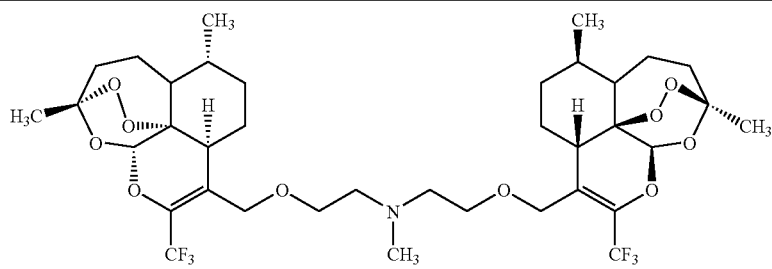
15
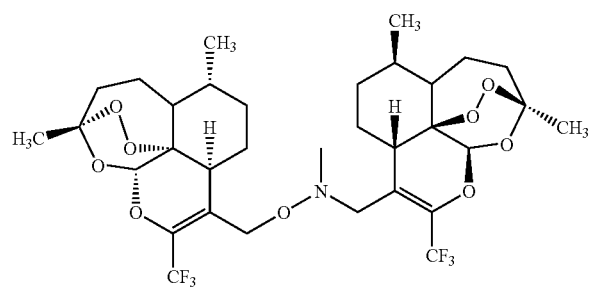
16
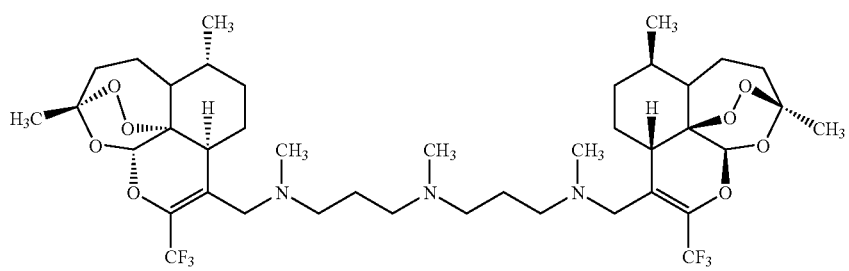
17
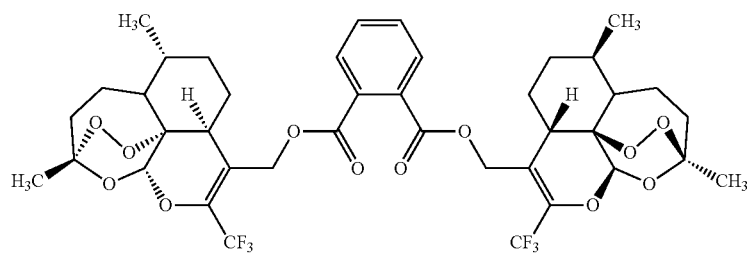
18
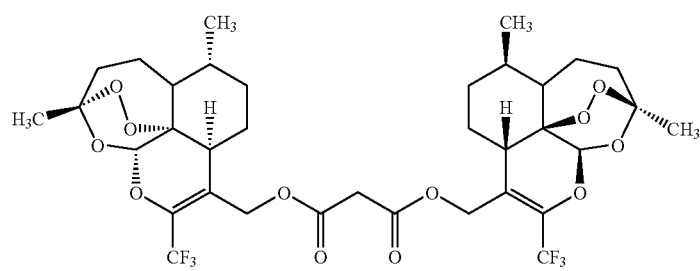
19
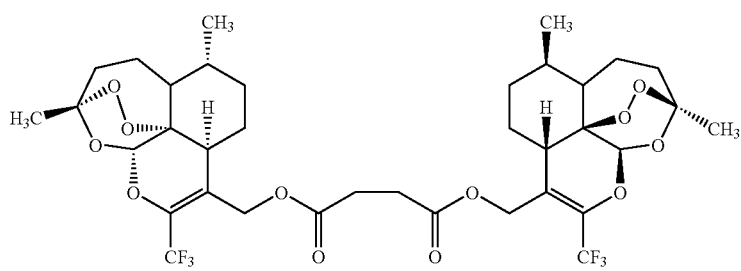

20
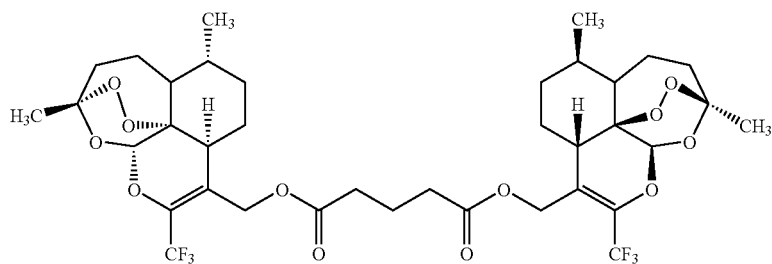
21
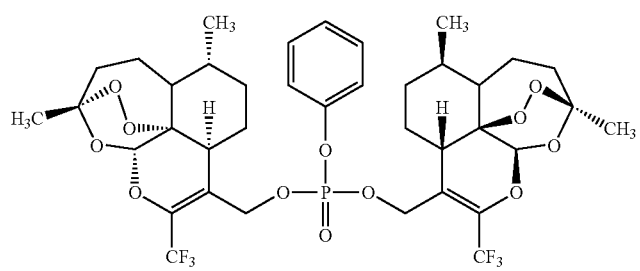
22
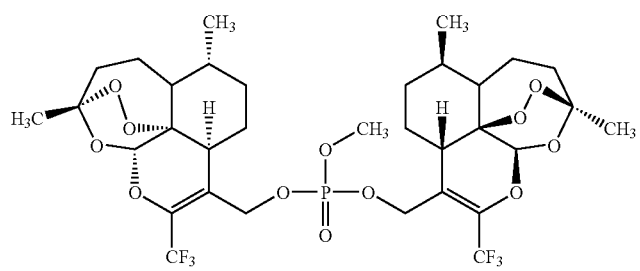
23
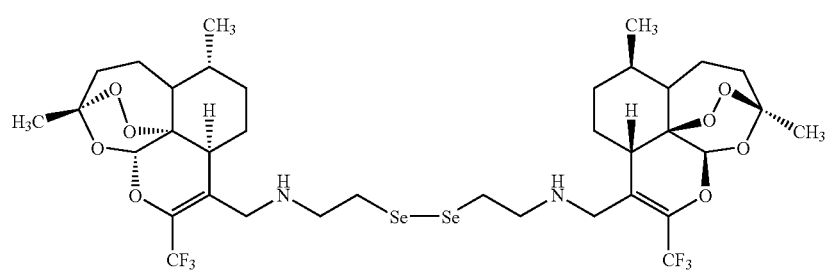
24
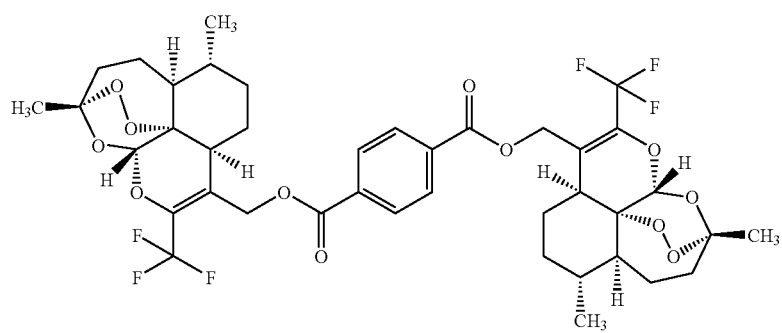

25
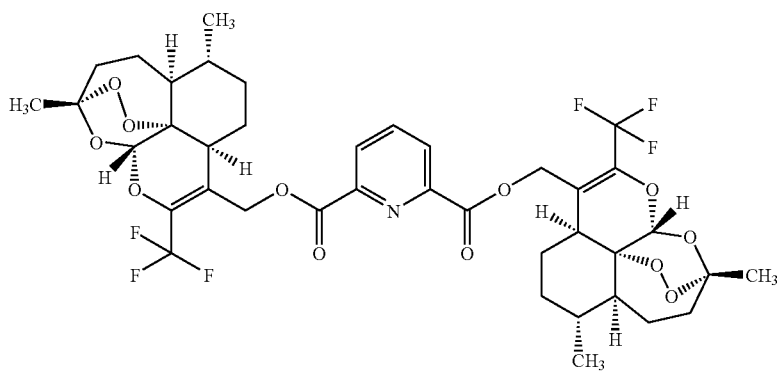
26
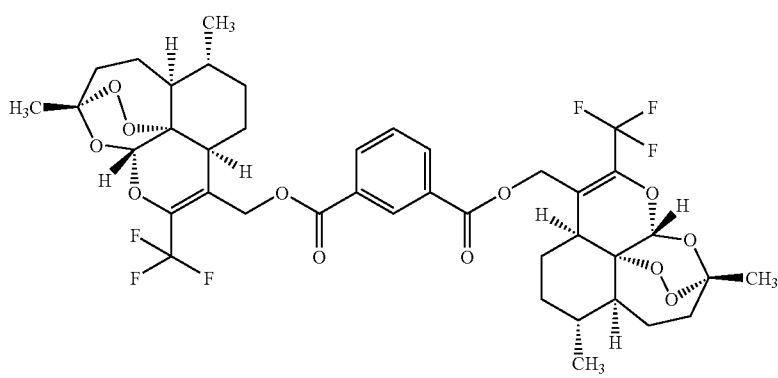
27
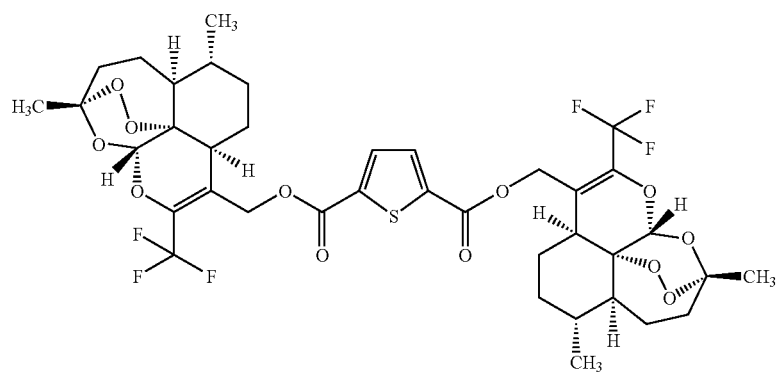
28
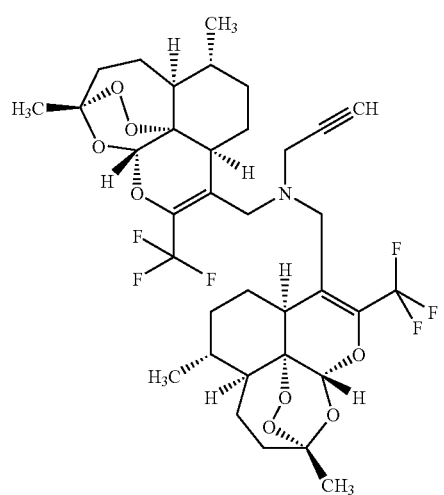

29 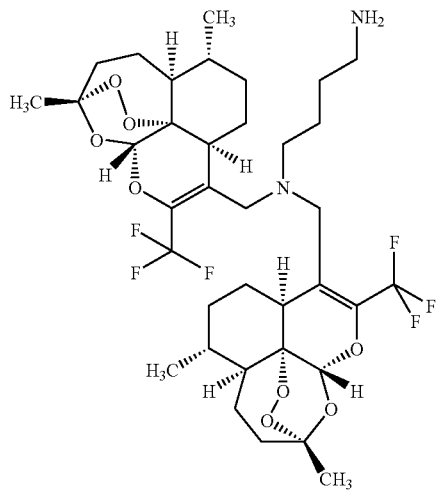
30 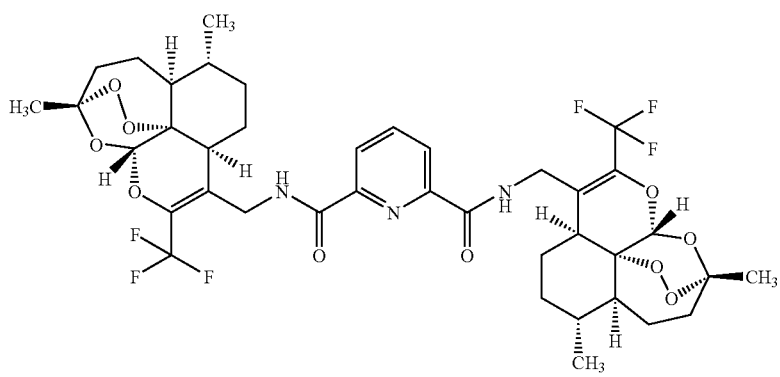
31 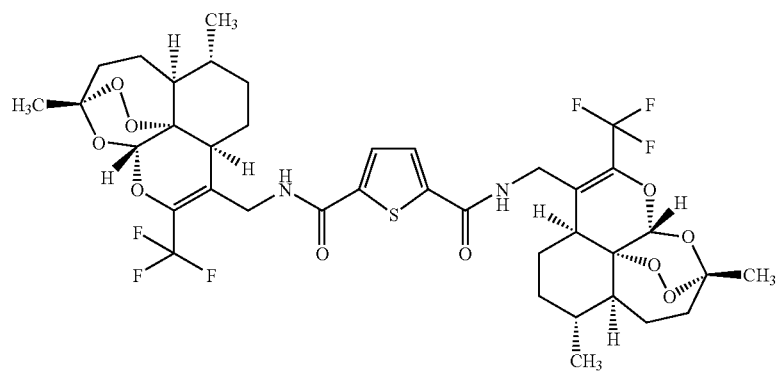
32 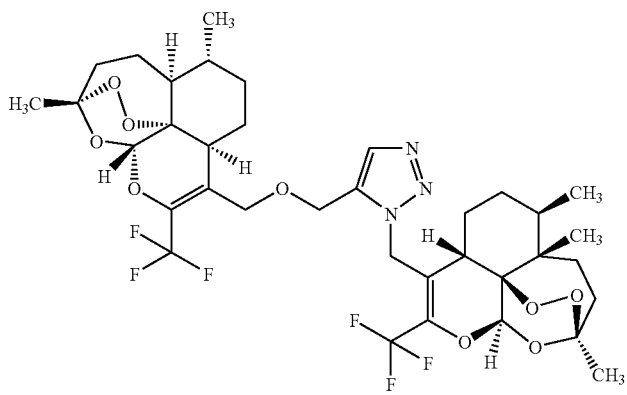

33 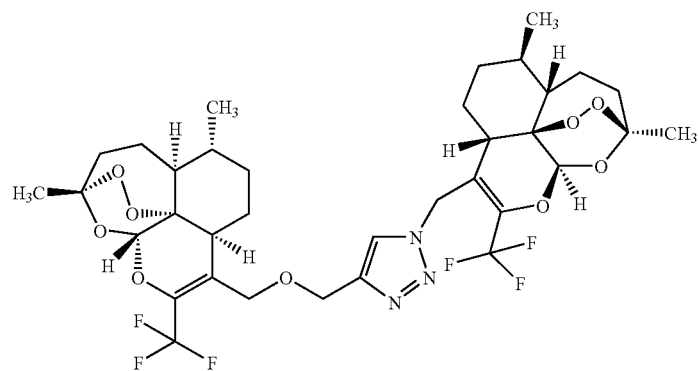
34 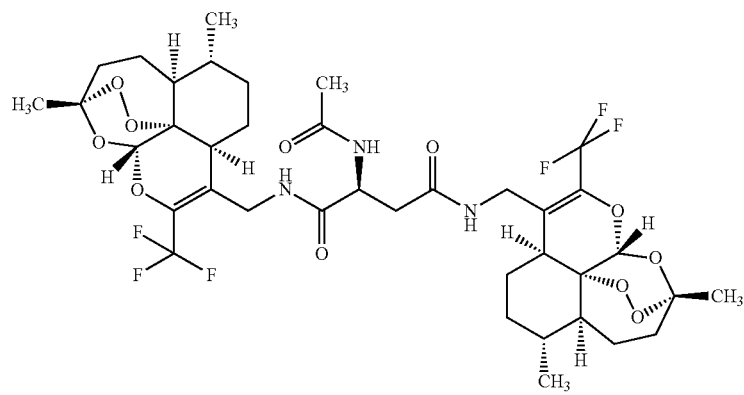
35 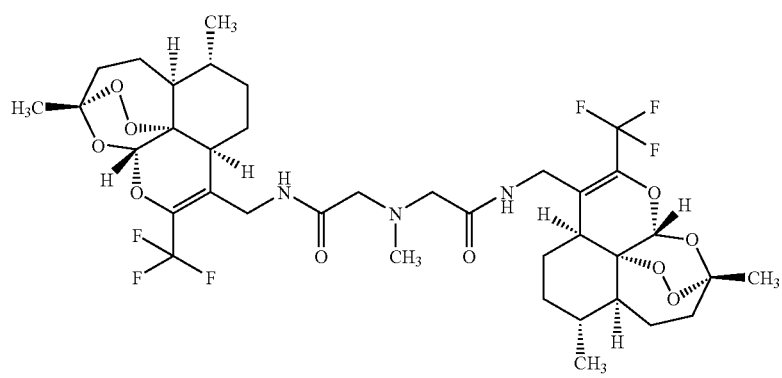
36 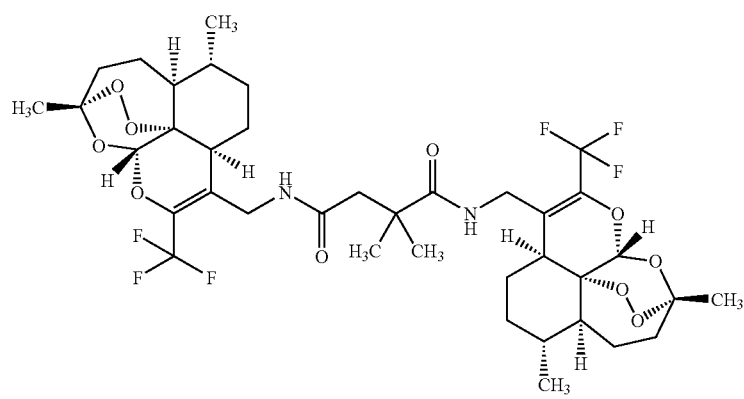

37 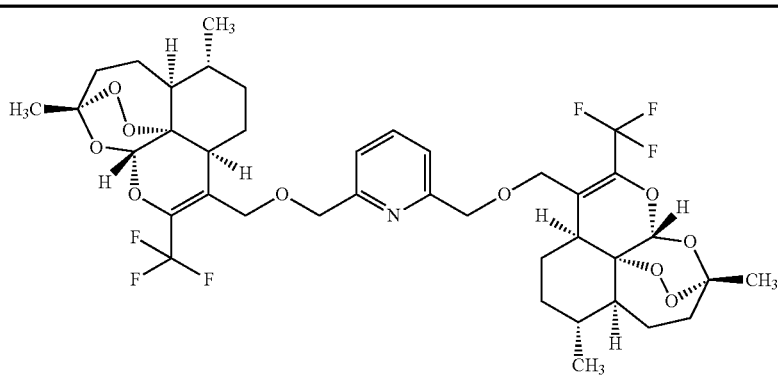

38 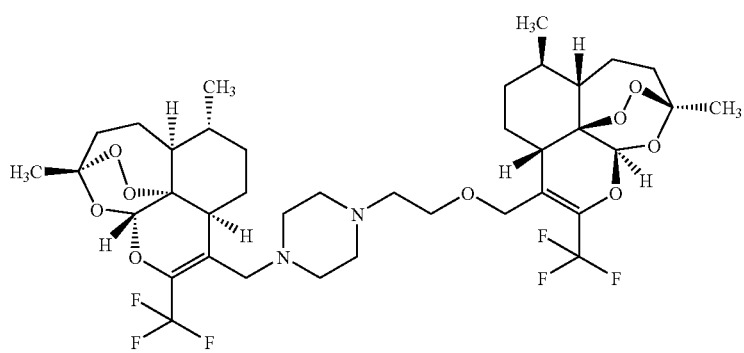

39 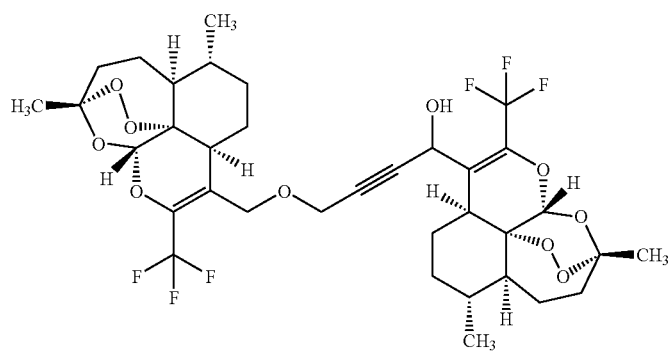

40 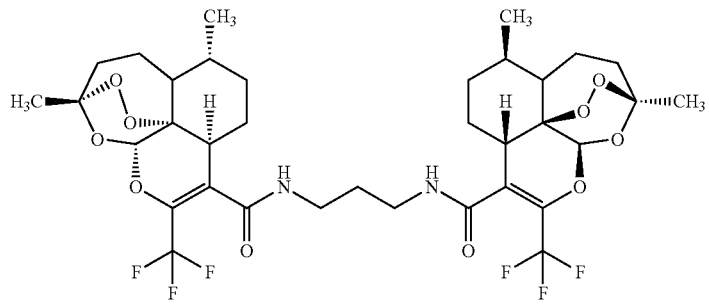

Cytotoxic Activity

Cytotoxic activity of the compounds prepared according to the invention was evaluated by measuring inhibition of cell proliferation of tumoral cell lines of human origin, such as the A549 cell line (lung) and the Namalwa cell line (lymphoma). This activity is expressed by $IC_{50}$, the concentration of the tested product capable of inhibiting cell proliferation by 50%. The method used is a measurement of residual ATP by luminescence after 72 hours of incubation by using the "ATPLite" kit marketed by Perkin Elmer.

As an example, cytotoxic properties of a few compounds of the invention (compounds nos. 1, 4, 5, 6, 8, 2, 9, 3, 7, 11, 12,

| | IC$_{50}$ (expressed in nM) | |
|---|---|---|
| Products | A549 | Namalwa |
| 1 | 200 | 290 |
| 4 | 84 | 64 |
| 5 | 90 | 50 |
| 6 | 63 | 27 |
| 8 | 270 | 64 |
| 2 | 850 | 1000 |
| 9 | 31 | 24 |
| 3 | 1200 | 2300 |
| 7 | 150 | 100 |
| 11 | 1100 | 790 |
| 12 | 690 | 390 |
| 33 | 110 | 30 |
| 26 | 71 | 54 |
| 25 | 140 | 62 |
| 30 | 170 | 72 |
| 31 | 220 | 88 |
| 27 | 210 | 130 |
| 32 | 270 | 130 |
| 37 | | 74 | 30 |
| 39 | 240 | 160 |

Taking into account these cytotoxic properties, the compounds of the invention may be used in human therapy in the treatment of cancer pathologies. Pharmaceutical preparations containing these active ingredients may be formulated for administration notably via an oral, intravenous or subcutaneous route.

The invention claimed is:

1. Dimeric derivative of 10-trifluoromethylated artemisinin of formula(I):

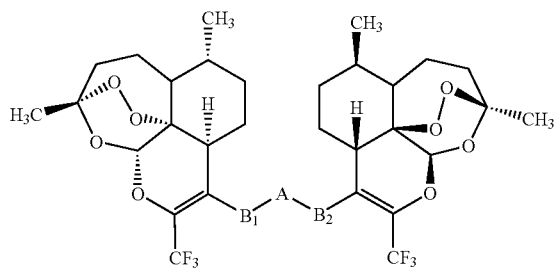

(I)

or a pharmaceutically acceptable salt thereof, for which:
  $B_1$ and $B_2$ are identical or different and selected from $C=O$, CHOH and $CH_2$, and
  A represents:
    a divalent group selected from —S—, and —S—S—.

2. The dimeric derivative according to claim 1, wherein $B_1$ and $B_2$ are identical or different and selected from $C=O$ and $CH_2$.

3. The dimeric derivative according to claim 2, wherein $B_1$ and $B_2$ each represent a $CH_2$ group.

4. The dimeric derivative according to claim 1, wherein it is selected from the following compounds:

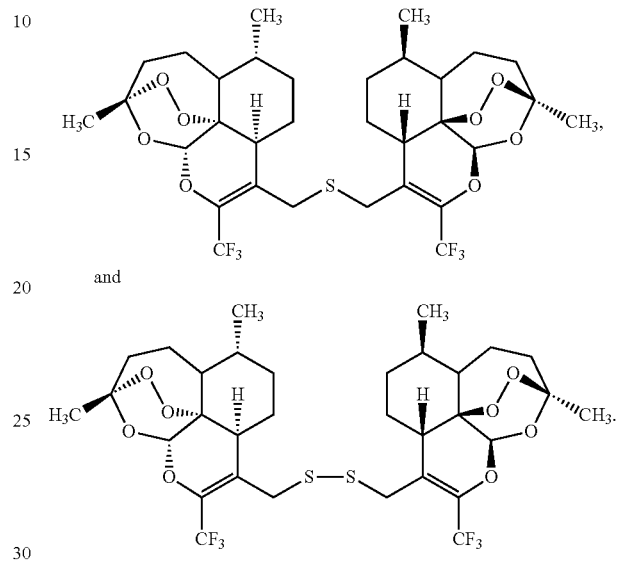

5. A pharmaceutical composition comprising at least one dimeric derivative according to claim 1 and at least one pharmaceutically acceptable carrier.

6. The pharmaceutical composition according to claim 5, further comprising another active ingredient.

7. The pharmaceutical composition according to claim 6, wherein the other active ingredient is selected from 6-mercaptopurine, fludarabine, cladribine, pentostatin, cytarabine, 5-fluorouracil, gemcitabine, methotrexate, raltitrexed, irinotecan, topotecan, etoposide, daunorubicin, doxorubicin, epirubicin, idarubicin, pirarubicin, mitoxantrone, chlormethine, cyclophosphamide, ifosfamide, melphalan, chlorambucil, busulfan, carmustine, fotemustine, streptozocin, carboplatin, cisplatin, oxaliplatin, procarbazine, dacarbazine, bleomycin, vinblastine, vincristine, vindesine, vinorelbine, paclitaxel, docetaxel, L-asparaginase, flutamide, nilutamide, bicalutamide, cyproterone acetate, triptorelin, leuprorelin, goserelin, buserelin, formestane, aminoglutethimide, anastrazole, letrozole, tamoxifen, octreotide and lanreotide.

8. A method for treating cancer comprising the administration of an effective amount of a dimeric derivative according claim 1 to a person in need thereof.

* * * * *

UNITED STATES PATENT AND TRADEMARK OFFICE
CERTIFICATE OF CORRECTION

PATENT NO. : 8,236,850 B2  
APPLICATION NO. : 12/808828  
DATED : August 7, 2012  
INVENTOR(S) : Jean-Pierre Begue et al.

Page 1 of 1

It is certified that error appears in the above-identified patent and that said Letters Patent is hereby corrected as shown below:

IN THE CLAIMS:

In claim 8, at column 58, lines 51-52, change "A method for treating cancer comprising the administration of" to --A method of treating lung or lymphoma cancer comprising administering--.

Signed and Sealed this  
Sixteenth Day of April, 2013

Teresa Stanek Rea  
*Acting Director of the United States Patent and Trademark Office*